United States Patent
DeKelver et al.

(10) Patent No.: US 9,045,763 B2
(45) Date of Patent: Jun. 2, 2015

(54) LINEAR DONOR CONSTRUCTS FOR TARGETED INTEGRATION

(75) Inventors: Russell DeKelver, La Jolla, CA (US);
Philip D. Gregory, Orinda, CA (US);
Michael C. Holmes, Oakland, CA (US);
Fyodor Urnov, Point Richmond, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 488 days.

(21) Appl. No.: 13/134,766

(22) Filed: Jun. 16, 2011

(65) Prior Publication Data

US 2011/0281361 A1 Nov. 17, 2011

Related U.S. Application Data

(63) Continuation of application No. 12/386,059, filed on Apr. 13, 2009, now abandoned, which is a continuation-in-part of application No. 11/493,423, filed on Jul. 26, 2006, now abandoned.

(60) Provisional application No. 61/124,047, filed on Apr. 14, 2008, provisional application No. 60/702,394, filed on Jul. 26, 2005, provisional application No. 60/721,054, filed on Sep. 26, 2005.

(51) Int. Cl.
*C07H 21/02* (2006.01)
*C07H 21/04* (2006.01)
*C12N 15/00* (2006.01)
*C12N 15/87* (2006.01)
*C12N 15/82* (2006.01)
*C12N 15/90* (2006.01)

(52) U.S. Cl.
CPC .......... *C12N 15/8213* (2013.01); *C12N 15/907* (2013.01)

(58) Field of Classification Search
None
See application file for complete search history.

(56) References Cited

U.S. PATENT DOCUMENTS

| | | | |
|---|---|---|---|
| 5,356,802 A | 10/1994 | Chandrasegaran | |
| 5,420,032 A | 5/1995 | Marshall | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo et al. | |
| 6,013,453 A | 1/2000 | Choo et al. | |
| 6,140,466 A | 10/2000 | Barbas et al. | |
| 6,200,759 B1 | 3/2001 | Dove et al. | |
| 6,242,218 B1 | 6/2001 | Treco et al. | |
| 6,242,568 B1 | 6/2001 | Barbas et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,506,559 B1 | 1/2003 | Driver et al. | |
| 6,528,313 B1 | 3/2003 | Le Mouellic et al. | |
| 6,528,314 B1 | 3/2003 | Le Mouellic et al. | |
| 6,534,261 B1 | 3/2003 | Cox et al. | |
| 6,833,252 B1 | 12/2004 | Dujon et al. | |
| 2002/0183275 A1 | 12/2002 | Murphy et al. | |
| 2003/0224521 A1 | 12/2003 | Court et al. | |
| 2003/0232410 A1 | 12/2003 | Liljedahl et al. | |
| 2005/0064474 A1 | 3/2005 | Urnov et al. | |
| 2005/0208489 A1 | 9/2005 | Carroll | |
| 2006/0063231 A1 | 3/2006 | Li et al. | |
| 2006/0188987 A1 | 8/2006 | Guschin et al. | |
| 2007/0117128 A1 | 5/2007 | Smith et al. | |
| 2008/0299580 A1 | 12/2008 | DeKelver et al. | |

FOREIGN PATENT DOCUMENTS

| | | |
|---|---|---|
| EP | 1311661 B1 | 3/2012 |
| GB | 2338237 A | 12/1999 |
| WO | WO 95/19431 A1 | 7/1995 |
| WO | WO 96/06166 A1 | 2/1996 |
| WO | WO 98/53059 A1 | 1/1998 |
| WO | WO 98/37186 A1 | 8/1998 |
| WO | WO 98/53057 A1 | 11/1998 |
| WO | WO 98/53058 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/53480 A1 | 7/2001 |
| WO | WO 01/60970 A2 | 8/2001 |
| WO | WO 01/88197 A2 | 11/2001 |
| WO | WO 02/16536 A2 | 2/2002 |
| WO | WO 02/057293 A2 | 7/2002 |
| WO | WO 02/077227 A2 | 10/2002 |
| WO | WO 02/099084 A2 | 12/2002 |

(Continued)

OTHER PUBLICATIONS

Yu, D. et al., "An efficient recombination system for chromosome engineering in *Escherichia coli*", PNAS, May, 2000, vol. 97: pp. 5978-5983.*
U.S. Appl. No. 61/189,800, "Methods and Compositions for Targeted Single-Strand Cleavage and Targeted Integration," filed Aug. 22, 2008.
Argast, et al., "I-PPOI and I-CREI Homing Site Sequence Degeneracy Determined by Random Mutagenesis and Sequential In Vitro Enrichment," *J. Mol. Biol.* 280:345-353 (1998).
Ashworth, et al., "Computational Redesign of Endonuclease DNA Binding and Cleavage Specificity," *Nature* 441:656-659 (2006).
Belfort, et al., "Homing Endonucleases: Keeping the House in Order," *Nucleic Acids Research* 25:3379-3388 (1997).
Bitinate, et al., "FOKI Dimerization is Required for DNA Cleavage," *PNAS USA* 95:10570-10575 (1998).
Capecchi, "Altering the Genome by Homologous Recombination," *Science* 244:1288-1292 (1989).

(Continued)

*Primary Examiner* — Michael Burkhart
(74) *Attorney, Agent, or Firm* — Pasternak Patent Law; Susan Abrahamson

(57) ABSTRACT

Disclosed herein are linear donor molecules comprising homology arms of 50-750 base pairs (e.g., 50-100 base pairs) flanking one or more sequences of interest. The donor molecules and/or compositions comprising these molecules can be used in methods for integration of an exogenous sequence into a specified region of interest in the genome of a cell.

23 Claims, 7 Drawing Sheets

(56) References Cited

FOREIGN PATENT DOCUMENTS

| WO | WO 03/016496 A2 | 2/2003 |
|---|---|---|
| WO | 2005014791 A2 | 2/2005 |
| WO | WO 2007/014275 A2 | 1/2007 |
| WO | WO 2008/021207 A2 | 2/2008 |
| WO | 2008133938 A2 | 6/2008 |

OTHER PUBLICATIONS

Chevalier, et al., "Design, Activity, and Structure of a Highly Specific Artificial Endonuclease," *Molecular Cell* 10:895-905 (2002).
Ciafre, et al., "Stability and Functional Effectiveness of Phosphorothioate Modified Duplex DNA and Synthetic Mini-Genes," *Nucleic Acids Res* 23(20):4134-4142 (1995).
Durai, et al., "Zinc Finger Nucleases:Cutom-Designed Molecular Scissors for Genome Engineering of Plant and Mammalian Cells," *Nucleic Acids Research* 33(18):5978-5990 (2005).
Dujon, et al., "Mobile Introns: Definition of Terms and Recommended Nomenclature," *Gene* 82:115-118 (1989).
Epinat, et al., "A Novel Engineered Meganuclease Induces Homologous Recombination in Yeast and Mammalian Cells," *Nucleic Acids Research* 31:2952-2962 (2003).
Gimble, et al., "Substrate Recognition and Induced DNA Distortion by the PI-SCEI Endonuclease, An Enzyme Generated by Protein Splicing," *J. Mol. Biol.* 263:163-180 (1996).
Jasin, et al., "Genetic Manipulation of Genomes With Rare-Cutting Endonucleases," *Trends Genet* 12:224-228 (1996).
Johansson, et al., "PCR-Generated Linear DNA Fragments Utilized as a Hantavirus DNA Vaccine," *Vaccine* 20(27-28):3379-3388 (2002).
Kim, et al., "Chimeric Restriction Endonuclease," *PNAS USA* 91:883-887 (1994).
Kim, et al., "Insertion and Deletion Mutants of FOKI Restriction Endonuclease," *J. Biol. Chem.* 269:31978-31981 (1994).
Li, et al., "Functional Domains in FOK I Restriction Endonuclease," *PNAS USA* 89:4275-4279 (1992).
Li, et al., "Alteration of the Cleavage Distance of FOK I Restriction Endonuclease by Insertion Mutagenesis," *PNAS USA* 90:2764-2768 (1993).
Miller, et al., "Repetitive Zinc-Binding Domains in the Protein Transcription Factor IIIA From Xenopus Oocytes," *EMBO J* 4:1609-1614 (1985).
Moehle, et al., "Targeted Gene Addition Into a Specified Location in the Human Genome Using Designed Zinc Finger Nucleases," *PNAS* 104:3055-3060 (2007).
Moore, et al., "Design of Polyzinc Finger Peptides With Structured Linkers," *PNAS USA* 98:1432-1436 (2001).
Moore, et al., "Improved DNA Binding Specificity From Polyzinc Finger Peptides by Using Strings of Two-Finger Units," *PNAS USA* 98:1437-1441 (2001).
Paques, et al., "Meganucleases and DNA Double-Strand Break-Induced Recombination: Perspectives for Gene Therapy," *Curr Gene Ther* 7:49-66 (2007).
Perler, et al., "Protein Splicing Elements: Inteins and Exteins a Definition of Terms and Recommended Nomenclature," *Nucleic Acids Research* 22:1125-1127 (1994).
Porteus, et al., "Gene Targeting Using Zinc Finger Nucleases," *Nature Biotechnology* 23:967-973 (2005).
Rhodes, "Zinc Fingers," *Scientific American* pp. 56-65 (1993).
Baudin, et al., "A Simple and Efficient Method for Direct Gene Deletion in Saccharomyces Cerevisiae," Nucleic Acids Research 21(14):3329-3330 (1993).
Cotta-de-Almeida, et al., "A New Method for Rapidly Generating Gene-Targeting Vectors by Engineering BACs Through Homologous Recombination in Bacteria," Genome Research 13:2190-2194 (2003).
Grzegorz et al., "Characterization of RAD51-Independent Break-Induced Replication That Acts Preferentially With Short Homologous Sequences," Molecular and Cellular Biology 20(23):6384-6392 (2002).
Lombardo, et al., Gene Editing in Human Stem Cells Using Zinc Finger Nucleases and Integrase-Defective Lentiviral Vector Delivery, Nature Biotechnology 25(11):1298-1306 (2007).
Miller, et al., An Improved Zinc-Finger Nulease Architecture for Highly Specific Genome Editing, Nature Biotechnology 25(7):778-785 2007.
Orlando, et al., "Supplemental Methods," Nucleic Acids Research 38(15):(2010).
Orlando, et al., "Zinc-Finger Nuclease-Driven Targeted Integration Into Mammalian Genomes Using Donors With Limited Chromosomal Homology," Nucleic Acids Research 38(15):e152 (2010).
Perez, et al., "Factors Affecting Double-Strand Break-Induced Homologous Recombination Into Mammalian Cells," BioTechniques 39(1):109-115 (2005).
Richardson, et al., "Coupled Homologous and Nonhomologous Repair of a Double-Strand Break Preserves Genomic Integrity in Mammalian Cells," Molecular and Cellular Biology 20(23):9068-9075 (2000).
Rouet, et al., "Expression of a Site-Specific Endonuclease Stimulates Homologous Recombination in Mammalian Cells," Proc. Natl. Acad. Sci. USA 91:6064-6068 (1994).
Urnov et al., "Highly Efficient Endogeneous Human Gene Correction Using Designed Zinc-Finger Nucleases," Nature 435:646-651(2005).

\* cited by examiner cctgtgtccccgagctgggaccacctatattcccagggccggttaatgtggctctggttctggtacttttatc
tgtccctccaccccacagtggggcaagctttctgacctctcttcctccccacagggcctcgagAGATCTGGCA
GCGGAGAGGGCAGAGGAAGTCTTCTAACATGCGGTGACGTGGAGGAGAATCCCGGCCCTAGGctcgagATGGTGA
GCAAGGGCGAGGAGCTGTTCACCGGGGTGGTGCCCATCCTGGTCGAGCTGGACGGCGACGTAAACGGCCACAAGT
TCAGCGTGTCCGGCGAGGGCGAGGGCGATGCCACCTACGGCAAGCTGACCCTGAAGTTCATCTGCACCACCGGCA
AGCTGCCCGTGCCCTGGCCCACCCTCGTGACCACCCTGACCTACGGCGTGCAGTGCTTCAGCCGCTACCCCGACC
ACATGAAGCAGCACGACTTCTTCAAGTCCGCCATGCCCGAAGGCTACGTCCAGGAGCGCACCATCTTCTTCAAGG
ACGACGGCAACTACAAGACCCGCGCCGAGGTGAAGTTCGAGGGCGACACCCTGGTGAACCGCATCGAGCTGAAGG
GCATCGACTTCAAGGAGGACGGCAACATCCTGGGGCACAAGCTGGAGTACAACTACAACAGCCACAACGTCTATA
TCATGGCCGACAAGCAGAAGAACGGCATCAAGGTGAACTTCAAGATCCGCCACAACATCGAGGACGGCAGCGTGC
AGCTCGCCGACCACTACCAGCAGAACACCCCCATCGGCGACGGCCCCGTGCTGCTGCCCGACAACCACTACCTGA
GCACCCAGTCCGCCCTGAGCAAAGACCCCAACGAGAAGCGCGATCACATGGTCCTGCTGGAGTTCGTGACCGCCG
CCGGGATCACTCTCGGCATGGACGAGCTGTACAAGTAAAGCGGCCATCTGTTGTTTGCCCCTCCCCCGTGCCTTC
CTTGACCCTGGAAGGTGCCACTCCCACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGGATTGGGAAGACAATAGCAGGCATGCTGGGGATG
CGGTGGGCTCTATGGtcgacagtactaagctttactagggacaggattggtgacagaaaagcccatcct tagg
cctcctcctcctagtcctcgatattggtctaaccccacctcctgttaggcagatt ttatattcccagggccggttaatgtggctctgtggttctggtactttatctgtccctccacccacagtgggcaa
gcttctgacctcttctcctcccacaggcctcgagAGATCTGGCAGCAAGGGCGAGGAGCGCAGAGGAAGTCTTCTAACA
TGCGGTGACGTGGAGGAGAATCCCGGCCCTAGGcctcgagATGGTGAGCAAGGGCGAGGAGCTGTTCACCGGGTGGT
GCCCATCCTGGTCGAGCTGGACGGCGACGTAAACGGCCACAAGTTCAGCGTGTCCGGCGAGGGCGAGGGCGATGCCA
CCTACGGCAAGCTGACCCTGAAGTTCATCTGCACCACCGGCAAGCTGCCCGTGCCCTGGCCCACCCTCGTGACCACC
CTGACCTACGGCGTGCAGTGCTTCAGCCGCTACCCCGACCACATGAAGCAGCACGACTTCTTCAAGTCCGCCATGCC
CGAAGGCTACGTCCAGGAGCGCACCATCTTCTTCAAGGACGACGGCAATACAAGACCCGCGCCGAGGTGAAGTTCG
AGGGCGACACCCTGGTGAACCGCATCGAGCTGAAGGGCATCGACTTCAAGGAGGACGGCAACATCCTGGGCACAAG
CTGGAGTACAACTACAACAGCCACAACGTCTATATCATGGCCGACAAGCAGAAGAACGGCATCAAGGTGAACTTCAA
GATCCGCCACAACATCGAGGACGGCAGCGTGCAGCTCGCCGACCACTACCAGCAGAACACCCCCATCGGCGACGGCC
CCGTGCTGCTGCCCGACAACCACTACCTGAGCACCCAGTCCGCCCTGAGCAAAGACCCCAACGAGAAGCGCGATCAC
ATGGTCCTGCTGGAGTTCGTGACCGCCGCCGGGATCACTCTCGGCATGGACGAGCTGTACAAGTAAAGCGGCCGCGT
CGAGTCTAGAGGGCCCGTTTAAACCCGCTGATCAGCCTCGACTGTGCCTTCTAGTTGCCAGCCATCTGTTGTTTGCC
CCTCCCCCGTGCCTTCCTTGACCCTGGAAGGTGCCACTCCCACTGTCCTTTCCTAATAAAATGAGGAAATTGCATCG
CATTGTCTGAGTAGGTGTCATTCTATTCTGGGGGGTGGGGTGGGGCAGGACAGCAAGGGGGAGGATTGGGAAGACAA
TAGCAGGCATGCTGGGGATGCGGTGGGCTCTATGGtcgacagtactaagctttactagggacaggattggtgacag
aaaagccccatccttaggcctcctccttagtctcctgatatattgggtccta AAVS1 75 bp HA (SEQ ID NO:2)

Fig. 3 ggctctggttctgggtactttatctgtcccctccacccacagtgggcaagcttctgacctcttcctcccaca
gggcctcgagAGATCTGGCAGCGGAGAGGGCAGAGGAAGTCTTCTAACATGCGGTGACGTGGAGGAGAATCCCGGCCCTA
GGctcgagATGGTGAGCAAGGGCGAGGAGCTGTTCACCGGGGTGGTGCCCATCCTGGTCGAGCTGGACGGCGACGTAAAC
GGCCACAAGTTCAGCGTGTCCGGCGAGGGCGAGGGCGATGCCACCTACGGCAAGCTGACCCTGAAGTTCATCTGCACCAC
CGGCAAGCTGCCCGTGCCCTGGCCCACCCTCGTGACCACCCTGACCTACGGCGTGCAGTGCTTCAGCCGCTACCCCGACC
ACATGAAGCAGCACGACTTCTTCAAGTCCGCCATGCCCGAAGGCTACGTCCAGGAGCGCACCATCTTCTTCAAGGACGAC
GGCAACTACAAGACCCGCGCCGAGGTGAAGTTCGAGGGCGACACCCTGGTGAACCGCATCGAGCTGAAGGGCATCGACTT
CAAGGAGGACGGCAACATCCTGGGGCACAAGCTGGAGTACAACTACAACAGCCACAACGTCTATATCATGGCCGACAAGC
AGAAGAACGGCATCAAGGTGAACTTCAAGATCCGCCACAACATCGAGGACGGCAGCGTGCAGCTCGCCGACCACTACCAG
CAGAACACCCCCATCGGCGACGGCCCCGTGCTGCTGCCCGACAACCACTACCTGAGCACCCAGTCCGCCCTGAGCAAAGA
CCCCAACGAGAAGCGCGATCACATGGTCCTGCTGGAGTTCGTGACCGCCGCTGATCAGCCTGACTGTGCCTTCTAGTTGCCAG
ACAAGTAAAGCGGCCGCGTCGAGTCTAGAGGGCCCGTTTAAACCCGCTGATCAGCCTCGACTGTGCCTTCTAGTTGCCAG
CCATCTGTTGTTTGCCCCTCCCCCGTGCCTTCCTTGACCCTGGAAGGTGCCACTCCCACTGTCCTTTCCTAATAAAATGA
GGAAATTGCATCGCATTGTCTGAGTAGGTGTCATTCTATTCTGGGGGGTGGGGTGGGGCAGGACAGCAAGGGGGAGGATT
GGGAAGACAATAGCAGGCATGCTGGGGATGCGGTGGGCTCTATGGtcgacagtactaagctttactaggacaggattg
gtgacagaaagcccatccttaggcctcctcct AAVS1 50 bp HA (SEQ ID NO:3)

Fig. 4 gtgtggatgggcagaaacgctacacgtttcgtgttcggagccgcttaacctcgatcgagaagcttgatatcgaat
tcccacggggttggggcttgcgccttttccaaggcagccctggtttgcgcaggacggcgctgctctgggcgtggt
tccgggaaacgcagcggcgccgaccctggtctcgcacattcttcacgtcgttcgcagcgtcacccgatcttcg
ccgctaccctgtgggccccccggcgacgcttcctgctccgccccctaagtcgggaaggttcctgcggttgcggc
gtgccggacgtgacaaacggaagccgacgctctcactagtaccctcgcagacgacagcgccaggagcaatggca
gcgcgccgaccgcgatgggcgtgtggccaatagcggctgctcagcggggcgcgccgagacgagcagcggaagggg
cggtgcgggaggcgacgtcggcagtgtgggcggtagtgtgggccctgttcctgccgcgcggtgttccgcattctgcaagcc
tccggagcgcacgtcggcagtcggctccctcgttgaccgaatcaccgacctctctcccagggatccaccggtc
gccaccATGGTGAGCAAGGGCGAGGAGCTGTTCACCGGGGTGGTGCCCATCCTGGTCGAGCTGGACGGCGACGTAA
ACGGCCACAAGTTCAGCGTGTCCGGCGAGGGCGATGCCACCTACGGCAAGCTGACCCTGAAGTTCATCTG
CACCACCGGCAAGCTGCCCGTGCCCTGGCCCACCCTCGTGACCACCCTGACCTACGGCGTGCAGTGCTTCAGCCGC
TACCCCGACCACATGAAGCAGCACGACTTCTTCAAGTCCGCCATGCCCGAAGGCTACGTCCAGGAGCGCACCATCT
TCTTCAAGGACGACGGCAACTACAAGACCCGCGCCGAGGTGAAGTTCGAGGGCGACACCCTGGTGAACCGCATCGA
GCTGAAGGGCATCGACTTCAAGGAGGACGGCAACATCCTGGGGCACAAGCTGGAGTACAACTACAACAGCCACAAC
GTCTATATCATGGCCGACAAGCAGAAGAACGGCATCAAGGTGAACTTCAAGATCCGCCACAACATCGAGGACGGCA
GCGTGCAGCTCGCCGACCACTACCAGCAGAACACCCCCATCGGCGACGGCCCCGTGCTGCTGCCCGACAACCACTA
CCTGAGCACCCAGTCCGCCCTGAGCAAAGACCCCAACGAGAAGCGCGATCACATGGTCCTGCTGGAGTTCGTGACC
GCCGCCGGGATCACTCTCGGCATGGACGAGCTGTACAAGTAAAGCGGCCATCTGTTGTTTGCCCCTCCCCCGTGCCTTCCTGAC
CCGCTGATCAGCCTCGACTGTGCCTTCTAGTTGCCAGCCATCGTTGTTTGCCCCTCGTGCCTTCCTTGAC
CCTGGAAGGTGCCACTCCCACTGTCCTTTCCTAATAAAATGAGGAAATTGCATCGCATTGTCTGAGTAGTGTCAT
TCTATTCTGGGGGGTGGGGTGGGGCAGGACAGCAAGGGGGAGGATTGGGAAGACAATAGCAGGCATGCTGGGGATG
CGGTGGGCTCTATGGcttctgaggcggaaagaaccagtcgagccactctgtggaagtgctcagcattggagtgaat
ggagccacccaatcca IL2R 50bpHA (SEQ ID NO:4)

Fig. 5

LINEAR DONOR CONSTRUCTS FOR TARGETED INTEGRATION

CROSS-REFERENCE TO RELATED APPLICATIONS

The present application is a continuation of U.S. patent application Ser. No. 12/386,059, filed Apr. 13, 2009 now abandoned, which claims the benefit of U.S. Provisional Application No. 61/124,047, filed Apr. 14, 2008. This application is also a continuation-in-part of U.S. application Ser. No. 11/493,423, filed Jul. 26, 2006 now abandoned, which claims the benefit of U.S. Provisional Application No. 60/702,394, filed Jul. 26, 2005 and U.S. Provisional Application No. 60/721,054, filed Sep. 26, 2005. All of the above-referenced disclosures are hereby incorporated by reference in their entireties.

STATEMENT OF RIGHTS TO INVENTIONS MADE UNDER FEDERALLY SPONSORED RESEARCH

Not applicable.

TECHNICAL FIELD

The present disclosure is in the field of genome engineering, particularly linear donor constructs for targeted integration into the genome of a cell.

BACKGROUND

A major area of interest in genome biology, especially in light of the determination of the complete nucleotide sequences of a number of genomes, is the targeted integration into genomic sequences. Attempts have been made to alter genomic sequences in cultured cells by taking advantage of the natural phenomenon of homologous recombination. See, for example, Capecchi (1989) Science 244:1288-1292; U.S. Pat. Nos. 6,528,313 and 6,528,314.

In addition, various methods and compositions for targeted cleavage of genomic DNA have been described. Such targeted cleavage events can be used, for example, to induce targeted mutagenesis, induce targeted deletions of cellular DNA sequences, and facilitate targeted recombination and targeted integration at a predetermined chromosomal locus. See, for example, United States Patent Publications. 20030232410; 20050208489; 20050026157; 20050064474; and 20060188987, and International Publication WO 2007/014275, the disclosures of which are incorporated by reference in their entireties for all purposes. For example, targeted integration using zinc finger nucleases has been demonstrated with circular (plasmid) DNAs having long (~750 base pair) homology arms. See, Moehle et al. (2007)Proc. Nat'l. Acad. Sci. USA 104(9):3055-3060.

However, there remains a need for additional compositions comprising shorter, linear exogenous polynucleotides that optionally can resist exonuclease degradation and use of these compositions in methods for targeted integration.

SUMMARY

The present disclosure provides linear exogenous (donor) nucleic acids, compositions comprising these nucleic acids and methods of making, and using these linear donor molecules. Generally, the donor molecules described herein have two homology arms of between about 50 and 100 base pairs flanking a sequence of interest.

The donor sequences can be integrated in a targeted manner into the genome of a cell, for example using zinc finger nucleases (ZFNs) and/or meganucleases. Integration of the exogenous nucleic acid sequences into the genome is facilitated by targeted double-strand cleavage of the genome (chromosome) in the region of interest. Cleavage is preferably targeted to the region of interest through the use of fusion proteins comprising a zinc finger binding domain, which is engineered to bind a sequence within the region of interest, and a cleavage domain or a cleavage half-domain. Such cleavage stimulates integration of exogenous polynucleotide sequences at or near the cleavage site.

In one aspect, described herein is a linear nucleic acid molecule (donor molecule) comprising homology arms of 50-100 base pairs flanking a sequence of interest is provided. In certain embodiments, the linear donor molecule stably persists in the cell into which it is introduced. In other embodiments, the linear donor molecule is modified to resist exonucleolytic cleavage, for example by placing one or more phosphorothioate phosphodiester bonds between one or more base pairs on the ends of the donor molecule.

The sequence of interest of the donor molecule may comprise one or more sequences encoding a functional polypeptide (e.g., a cDNA), with or without a promoter. In certain embodiments, the nucleic acid sequence comprises a promoterless sequence encoding an antibody, an antigen, an enzyme, a growth factor, a receptor (cell surface or nuclear), a hormone, a lymphokine, a cytokine, a reporter, functional fragments of any of the above and combinations of the above. Expression of the integrated sequence is then ensured by transcription driven by an endogenous promoter or other control element in the region of interest. In other embodiments, a "tandem" cassette is integrated into the selected site in this manner, the first component of the cassette comprising a promotorless sequence as described, above, followed by a transcription termination sequence, and a second sequence, encoding an autonomous expression cassette. Additional sequences (coding or non-coding sequences) may be included in the donor molecule between the homology arms, including but not limited to, sequences encoding a 2A peptide, SA site, IRES, etc.

The donor molecules of the disclosure can be inserted into a specified location in a genome following cleavage of the genome, for example using one or more fusion molecules comprising a DNA-binding domain targeted to the specified location in the genome and a cleavage domain (e.g., a zinc finger nuclease (ZFN) or naturally or non-naturally occurring meganuclease to a particular locus. Thus, in another aspect, provided herein is a method for integrating an exogenous sequence as described herein into a region of interest in the genome of a cell, the method comprising: (a) expressing a fusion protein in the cell, the fusion protein comprising a DNA-binding domain (e.g., zinc finger binding domain) and a cleavage domain or cleavage half-domain, wherein the DNA-binding domain (e.g., zinc finger binding domain) has been engineered to bind to a target site in the region of interest in the genome of the cell; and (b) contacting the cell with a donor polynucleotide as described herein, wherein binding of the fusion protein to the target site cleaves the genome of the cell in the region of interest, thereby resulting in integration of the exogenous sequence into the genome of the cell within the region of interest.

In certain embodiments, the methods comprise the steps of (a) expressing a first fusion protein in the cell, the first fusion protein comprising a first zinc finger binding domain and a first cleavage half-domain, wherein the first zinc finger binding domain has been engineered to bind to a first target site in the region of interest in the genome of the cell; (b) expressing a second fusion protein in the cell, the second fusion protein comprising a second zinc finger binding domain and a second cleavage half domain, wherein the second zinc finger binding domain binds to a second target site in the region of interest in the genome of the cell, wherein the second target site is different from the first target site; and (c) contacting the cell with a exogenous donor molecule as described herein, wherein binding of the first fusion protein to the first target site, and binding of the second fusion protein to the second target site, positions the cleavage half-domains such that the genome of the cell is cleaved in the region of interest, thereby resulting in integration of the exogenous donor molecule into the genome of the cell within the region of interest.

In any of the methods described herein, the donor polynucleotide comprises a sequence encoding a functional polypeptide, which sequence is inserted into the genome of the cell.

Furthermore, in any of the methods described herein, the first and second cleavage half-domains are from a Type IIS restriction endonuclease, for example, FokI or StsI. Furthermore, in any of the methods described herein, at least one of the fusion proteins may comprise an alteration in the amino acid sequence of the dimerization interface of the cleavage half-domain, for example such that obligate heterodimers of the cleavage half-domains are formed. Alternatively, in any of the methods described herein the cleavage domain may be a naturally or non-naturally occurring meganuclease.

In any of the methods described herein, the cell can be a mammalian cell, for example, a human, rat, mouse or rabbit cell, or a plant cell. Additionally, the cell may be derived from an insect, xenopus or nematode system. Furthermore, the cell may be arrested in the G2 phase of the cell cycle.

The present subject matter thus includes, but is not limited to, the following embodiments:

1. A linear donor nucleic acid molecule comprising homology arms of between 50 and 750 base pairs and a sequence of interest, wherein the homology arms flank the sequence of interest.

2. The linear donor nucleic acid of 1, wherein the homology arms are between 50 and 100 base pairs in length.

3. The linear donor nucleic acid of 1, wherein one or more of the base pairs of the homology arms are joined with a phosphorothioate phosphodiester bond.

4. The linear donor nucleic acid of 3, wherein the phosphorothioate phosphodiester bonds are positioned at the first and, optionally, second bonds of the 5' and 3' ends of the donor nucleic acid.

5. The linear donor nucleic acid of any of 1 to 4, further comprising, between the homology arms, a sequence encoding a 2A peptide.

6. The linear donor nucleic acid of any of 1 through 5, further comprising, between the homology arms, a sequence comprising an SA site.

7. The linear donor nucleic acid of any of 1 through 6, further comprising, between the homology arms, a sequence comprising an IRES sequence.

8. The linear donor nucleic acid of any of 1 to 7, wherein the sequence of interest does not encode a polypeptide.

9. The linear donor nucleic acid of any of 1 to 7, further comprising a promoter sequence operably linked to the sequence of interest.

10. The linear donor nucleic acid of any of 1 to 7 or 9, wherein the sequence of interest encodes a polypeptide.

11. The linear donor nucleic acid according to 10, wherein the polypeptide is selected from the group consisting of an antibody, an antigen, an enzyme, a growth factor, a receptor (cell surface or nuclear), a hormone, a lymphokine, a cytokine, a reporter gene, a selectable marker, a secreted factor, an epitope tag and functional fragments thereof and combinations thereof.

12. The linear donor nucleic acid of any of 1 to 7 or 9, wherein the sequence contains a non-coding nucleic acid.

13. The linear donor nucleic acid according to claim 12 wherein the non-coding nucleic acid is selected from the group consisting of a miRNA, and SH-RNA, or siRNA.

14. A method for homology-dependent targeted integration of a sequence of interest into a region of interest in the genome of the cell, the method comprising the steps of:
(a) expressing a fusion protein in the cell, the fusion protein comprising a DNA-binding domain and cleavage domain or a cleavage half-domain, wherein the DNA-binding domain has been engineered to bind to a target site in the region of interest;
(b) contacting the cell with a donor polynucleotide of any of 1 to 11,
wherein binding of the fusion protein to the target site cleaves the genome of the cell in the region of the interest, thereby resulting in homology-dependent targeted integration of the sequence of interest into the genome of the cell.

15. A method for homology-dependent targeted integration of a sequence of interest into a cell, the method comprising:
(a) expressing a first fusion protein in the cell, the first fusion protein comprising a first DNA-binding domain and a first cleavage half-domain, wherein the first DNA-binding domain has been engineered to bind to a first target site in a region of interest in the genome of the cell;
(b) expressing a second fusion protein in the cell, the second fusion protein comprising a second DNA-domain and a second cleavage half domain, wherein the second zinc finger binding domain binds to a second target site in the region of interest in the genome of the cell, wherein the second target site is different from the first target site; and
(c) contacting the cell with a polynucleotide comprising a donor nucleic acid according to any of 1-11;
wherein binding of the first fusion protein to the first target site, and binding of the second fusion protein to the second target site, positions the cleavage half-domains such that the genome of the cell is cleaved in the region of interest, thereby resulting in homology-dependent integration of the donor nucleic said into the genome of the cell.

16. The method of 14 or 15, wherein at least one DNA-binding domain is a zinc finger binding domain.

17. The method of 14 to 16, wherein at least one DNA-binding domain is a meganuclease DNA-binding domain.

18. The method of 14 or 17, wherein the sequence of interest from the integrated donor nucleic acid expresses a polypeptide.

19. The method of 14 or 17 wherein the sequence in interest from the integrated donor comprises a non-coding nucleic acid sequence.

20. The method of 14 to 19, wherein the cleavage domain is from a meganuclease.

21. The method according to any of 14 to 19, wherein the first and second cleavage half-domains are from a Type IIS restriction endonuclease.

22. The method according to 21, wherein the Type IIS restriction endonuclease is selected from the group consisting of FokI and StsI.

23. The method according to any of 14 to 22, wherein the cell is arrested in the G2 phase of the cell cycle.

24. The method according to any of 14 to 23, wherein at least one of the fusion proteins comprises an alteration in the amino acid sequence of the dimerization interface of the cleavage half-domain.

25. The method according to any of 14 to 24, wherein the cell is a mammalian cell.

26. The method according to 25, wherein the cell is a human cell.

27. The method according to any of 14 to 24 wherein the cell is a plant cell.

28. The method according to any of 14 to 24 wherein the cell is a xenopus, insect or nematode cell.

BRIEF DESCRIPTION OF THE DRAWINGS

FIG. 2 depicts the sequence of an exemplary linear donor (SEQ ID NO:1) having homology arms of 100 base pairs. The linear donor molecule comprises a left homology arm from nucleotides 1 to 100 (lowercase, underlined); a splice acceptor (SA) site, from nucleotides 107 to 132 (lowercase, bold); a sequence encoding a foot-in-mouth-disease virus (FMDV)-derived 2A self-processing sequence (2A peptide) from nucleotides 141 to 212 (uppercase, no underlining); a sequence encoding green fluorescent protein (GFP) poly(A) from nucleotides 219 to 1,215 (uppercase, underlined); and a right homology arm from nucleotides 1235 to 1334 (lowercase, underlined).

FIG. 3 depicts the sequence of an exemplary linear donor (SEQ ID NO:2) having homology arms of 75 base pairs. The linear donor molecule comprises a left homology arm from nucleotides 1 to 75 (lowercase, underlined); an SA site from nucleotides 82 to 107 (lowercase, bold); a sequence encoding a 2A peptide from nucleotides 116 to 187 (uppercase, no underlining); a sequence encoding GFP poly(A) from nucleotides 194 to 1,190 (uppercase, underlined); and a right homology arm from nucleotides 1210 to 1284 (lowercase, underlined).

FIG. 4 depicts the sequence of an exemplary linear donor (SEQ ID NO:3) having homology arms of 50 base pairs. The linear donor molecule comprises a left homology arm from nucleotides 1 to 50 (lowercase, underlined); an SA site from nucleotides 57 to 82 (lowercase, bold); a sequence encoding a 2A peptide from nucleotides 91 to 162 (uppercase, no underlining); a sequence encoding GFP poly(A) from nucleotides 169 to 1,165 (uppercase, underlined); and a right homology arm from nucleotides 1,185 to 1,234 (lowercase; underlined).

FIG. 5 depicts the sequence of another exemplary linear donor (SEQ ID NO:4) having homology arms of 50 base pairs. The linear donor molecule comprises a left homology arm from nucleotides 1 to 50 (lowercase, underlined); an hPGK promoter sequence from nucleotides 79 to 594 (lowercase, bold); a sequence encoding GFP poly(A) from nucleotides 615 to 1,611 (uppercase, underlined); and a right homology arm from nucleotides 1,639 to 1,688 (lowercase, underlined).

DETAILED DESCRIPTION

Figure 1:
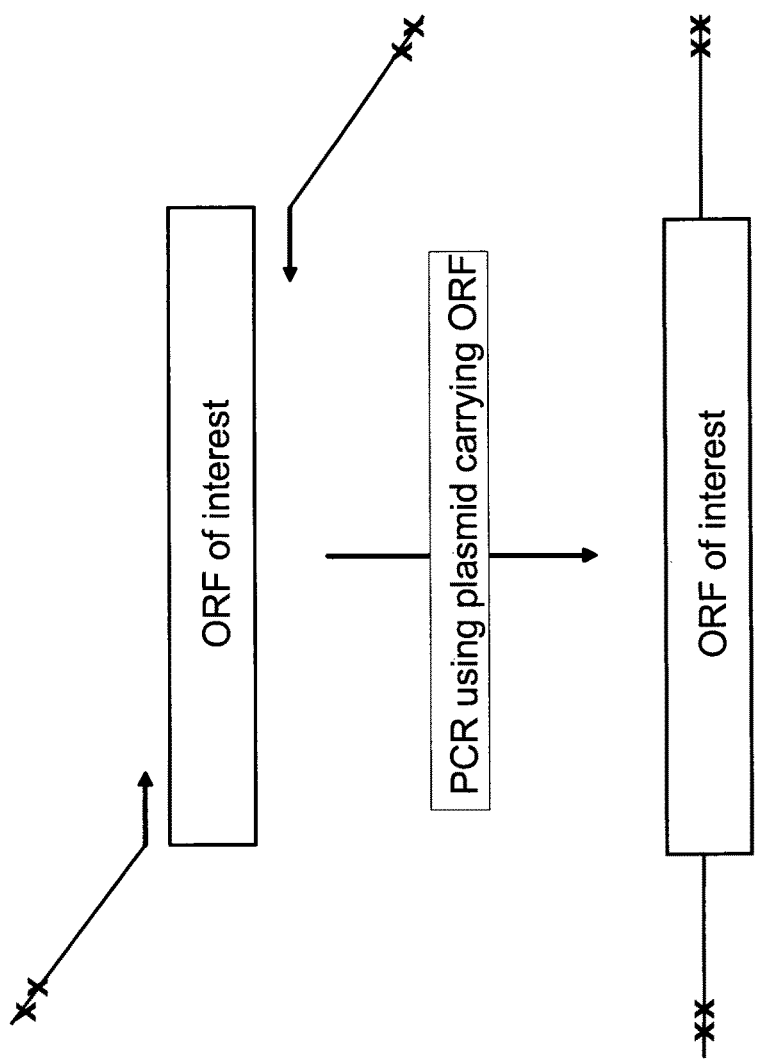
FIG. 1 is a schematic diagram depicting construction of a linear donor polynucleotide as described herein. The "x" denotes phosphorothioate phosphodiester bonds as the first and second bonds on the 5' and 3' ends of the polynucleotide.

The present disclosure relates to exogenous (donor) polynucleotides useful for homology-dependent targeted integration (TI) into a region of interest in a genome. In particular, the donor polynucleotides described herein are linear molecules comprising homology arms (HA) of approximately 50-100 base pairs. The homology arms flank one or more sequences of interest to be inserted into the genome of a cell. These donor molecules are useful for targeted cleavage and recombination into a specified region of interest in a genome when used in combination with fusion proteins (zinc finger nucleases) comprising a cleavage domain (or a cleavage half-domain) and a zinc finger binding domain (and/or polynucleotides encoding these proteins). A zinc finger binding domain can comprise one or more zinc fingers (e.g., 2, 3, 4, 5, 6, 7, 8, 9 or more zinc fingers), and can be engineered to bind to any sequence within the region of interest. In the presence of ZFPs, the linear donor polynucleotides described are integrated at high rates into the cleavage site by homology-dependent methods.

Advantages of the linear donor molecules described herein include the rapid and efficient provision of donor molecules for use with ZFNs. Currently, donor molecules used in combination with zinc finger nucleases (ZFNs) for targeted insertion into a specified locus of the genome are plasmid constructs containing long (~750 base pairs) homology arms flanking a transgene of interest. Construction of such plasmid donors is time-consuming, taking at least 2 weeks. By contrast, the linear donor molecules described herein can be constructed within hours and used immediately. In addition, use of linear donors as described herein reduces or eliminates the phenomena of stable insertion of the plasmid donor into the host cell.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form.

For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For, example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the internet. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at leak about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "cleavage half-domain" is a polypeptide sequence which, in conjunction with a second polypeptide (either identical or different) forms a complex having cleavage activity (preferably double-strand cleavage activity).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a coding sequence for any polypeptide or fragment thereof, a functioning version of a malfunctioning endogenous molecule or a malfunctioning version of a normally-functioning endogenous molecule. An exogenous molecule can also be the same type of molecule as an endogenous molecule but be derived from a different species than the species the endogenous molecule is derived from. For example, a human nucleic acid sequence may be introduced into a cell line originating from a hamster or mouse.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Exogenous nucleic acid molecules that can be targeted for insertion into a genome are also referred to as "donor" polynucleotides. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Eukaryotic" cells include, but are not limited to, fungal cells (such as yeast), plant cells, animal cells, mammalian cells and human cells.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant and/or from any stage of plant development.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Exogenous (Donor) Polynucleotides

Described herein are polynucleotides for insertion into the genome, also referred to as "exogenous" polynucleotides or "donor" polynucleotides. It has been shown that plasmid donors carrying 750 bp homology arms flanking a transgene of interest, in combination with designed zinc finger nucleases (ZFNs) can be used for targeted gene alteration. See, e.g., Moehle et al. (2007)*Proc. Nat'l. Acad. Sci. USA* 104(9):3055-3060 and U.S. Patent Publication No. 20050064474. Constructing such plasmid donor polynucleotides with long homology arms is a time-consuming procedure, involving: design PCR primers that amplify an ~4.5 kb fragment of the locus of interest; identification (by amplification, cloning and sequencing) of a single clone carrying the desired fragment and lacking PCR-induced mutations; introduction (typically by site-directed mutagenesis) of a unique RFLP into the center of that fragment; cloning of the ORF of interest into that fragment; identification (typically by restriction digest) of a clone carrying the ORF in the desired orientation; and amplification of the plasmid to sufficient quantities for use in targeted genomic alteration. Under the best circumstances, this process takes approximately two weeks and results in a circular (plasmid) donor polynucleotide.

Surprisingly, we demonstrate herein that linear donor sequences of the disclosure comprising short homology arms of approximately 50-100 base pairs can be effectively integrated into the genome of cell. The linear donor sequences described herein take only hours to construct.

In certain embodiments, the linear donor sequences described herein are 25 to 50 base pairs in length (or any value therebetween, including 26, 27, 28, 29, 30, 31, 32, 33, 34, 35, 36, 37, 38, 39, 40, 41, 42, 43, 44, 45, 46, 47, 48, 49 or 50 nucleotides). In other embodiments, the sequences are between 50 and 75 nucleotides in length (including 50, 51, 52, 53, 54, 55, 56, 57, 58, 59, 60, 61, 62, 63, 64, 65, 66, 67, 68, 69, 70, 71, 72, 73, 74 or 75 nucleotides in length). In still other embodiments, the sequences are between 75 and 100 nucleotides in length (including 75, 76, 77, 78, 79, 80, 81, 82, 83, 84, 85, 86, 87, 88, 89, 90, 91, 92, 93, 94, 95, 96, 97, 98, 99, or 100 nucleotides in length). In still other embodiments, the donor polynucleotides are between 100 and 150 nucleotides in length (or any value therebetween). In other embodiments, the donor polynucleotides are between 50 and 750 nucleotides in length (e.g., 50 and 100, 50 and 150, 50 and 200, 50 and 250, 50 and 300, 50 and 350, 50 and 400, 50 and 450, 50 and 500, 50 and 550, 50 and 600, 50 and 650, 50 and 700).

The donor sequences described herein may be isolated from plasmids, cells or other sources using standard techniques known in the art such as PCR. Alternatively, they may be chemically synthesized using standard oligonucleotide synthesis techniques. Typically, the donor polynucleotides are made by PCR using a primer with a 50-100 bp 5' portion homologous to the genomic target, and a 15-18 bp portion identical to the ORF of interest (FIG. 1).

The linear donor polynucleotides described herein may include one or more phosphorothioate phosphodiester bonds between terminal base pairs to protect the linear donor polynucleotide from exonucleolytic degradation. These bonds may be in two or more positions at the 5' and/or 3' ends of the molecule and may be added during isolation or synthesis using standard methodology. See, e.g., Ciafre et al. (1995) *Nucleic Acids Res.* 23(20):4134-42; Johansson et al. (2002) *Vaccine* 20(27-28):3379-88. In embodiments in which the donor polynucleotide is isolated by PCR using primers (FIG. 1), the 5' ends of the primer (and donor polynucleotide) are typically phosphorothioate phosphodiester bonds. Alternatively, the linear donor polynucleotides may include one or more 5' deoxynucleotides, biotin and/one or more amine groups, all of which have been shown to reduce exonucleolytic degradation.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites, epitope tags and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

The exogenous (donor) polynucleotide may also comprise sequences which do not encode polypeptides but rather any type of noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

A donor molecule can contain several, discontinuous regions of homology to cellular chromatin. For example, the regions of homology can flank two or more regions containing the desired alterations. In a preferred embodiment, the exogenous sequence comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

A donor molecule can be a linear molecule following linearization, as a result of ZFN directed cleavage, of a plasmid taken up by a cell. In another embodiment, the linear donor molecule can reside in the genome of the cell wherein the donor molecule becomes available for homology directed targeted integration following ZFN directed cleavage and release of the donor from the genome.

For example, the exogenous sequence may comprise a sequence encoding a polypeptide that is lacking or non-functional in the subject having a genetic disease, including but not limited to any of the following genetic diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefelter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeriao, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted integration include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Furthermore, although not required for expression, exogenous sequences may also transcriptional or translational regulatory sequences, for example, promoters, enhancers, insulators, internal ribosome entry sites, sequences encoding 2A peptides, and/or polyadenylation signals.

Target Sites

The disclosed methods and compositions include fusion proteins comprising a cleavage domain (or a cleavage half-domain) and a zinc finger domain, in which the zinc finger domain, by binding to a sequence a region of interest in the genome of a cell directs the activity of the cleavage domain (or cleavage half-domain) to the vicinity of the sequence and, hence, induces cleavage (e.g., a double stranded break) in the region of interest. As set forth elsewhere in this disclosure, a zinc finger domain can be engineered to bind to virtually any desired sequence. Accordingly, one or more zinc finger binding domains can be engineered to bind to one or more sequences in the region of interest. Expression of a fusion protein comprising a zinc finger binding domain and a cleavage domain (or of two fusion proteins, each comprising a zinc finger binding domain and a cleavage half-domain), in a cell, effects cleavage in the region of interest.

Selection of a sequence in a region of interest for binding by a zinc finger domain (e.g., a target site) can be accomplished, for example, according to the methods disclosed in co-owned U.S. Pat. No. 6,453,242 (Sep. 17, 2002), which also discloses methods for designing ZFPs to bind to a selected sequence. It will be clear to those skilled in the art that simple visual inspection of a nucleotide sequence can also be used for selection of a target site. Accordingly, any means for target site selection can be used in the methods described herein.

Target sites are generally composed of a plurality of adjacent target subsites. A target subsite refers to the sequence (usually either a nucleotide triplet, or a nucleotide quadruplet that can overlap by one nucleotide with an adjacent quadruplet) bound by an individual zinc finger. See, for example, WO 02/077227. If the strand with which a zinc finger protein makes most contacts is designated the target strand "primary recognition strand," or "primary contact strand," some zinc finger proteins bind to a three base triplet in the target strand and a fourth base on the non-target strand. A target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

It is not necessary for a target site to be a multiple of three nucleotides. For example, in cases in which cross-strand interactions occur (see, e.g., U.S. Pat. No. 6,453,242 and WO 02/077227), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a 13-nucleotide sequence, wherein the thirteenth nucleotide is part of a quadruplet bound by a terminal finger, etc.

The length and nature of amino acid linker sequences between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. No. 6,479,626 and WO 01/53480. Accordingly, one or more subsites, in a target site for a zinc finger binding domain, can be separated from each other by 1, 2, 3, 4, 5 or more nucleotides. To provide but one example, a four-finger binding domain can bind to a 13-nucleotide target site comprising, in sequence, two contiguous 3-nucleotide subsites, an intervening nucleotide, and two contiguous triplet subsites.

Distance between sequences (e.g., target sites) refers to the number of nucleotides or nucleotide pairs intervening between two sequences, as measured from the edges of the sequences nearest each other.

In certain embodiments in which cleavage depends on the binding of two zinc finger domain/cleavage half-domain fusion molecules to separate target sites, the two target sites can be on opposite DNA strands (Example 1). In other embodiments, both target sites are on the same DNA strand.
DNA Binding Domains Any DNA-binding domain can be used in the methods disclosed herein. In certain embodiments, the DNA binding domain comprises a zinc finger protein. A zinc finger binding domain comprises one or more zinc fingers. Miller et al. (1985) *EMBO J.* 4:1609-1614; Rhodes (1993)*Scientific American* Feb.:56-65; U.S. Pat. No. 6,453,242. The zinc finger binding domains described herein generally include 2, 3, 4, 5, 6 or even more zinc fingers.

Typically, a single zinc finger domain is about 30 amino acids in length. Structural studies have demonstrated that each zinc finger domain (motif) contains two beta sheets (held in a beta turn which contains the two invariant cysteine residues) and an alpha helix (containing the two invariant histidine residues), which are held in a particular conformation through coordination of a zinc atom by the two cysteines and the two histidines.

Zinc fingers include both canonical $C_2H_2$ zinc fingers (i.e., those in which the zinc ion is coordinated by two cysteine and two histidine residues) and non-canonical zinc fingers such as, for example, $C_3H$ zinc fingers (those in which the zinc ion is coordinated by three cysteine residues and one histidine residue) and $C_4$ zinc fingers (those in which the zinc ion is coordinated by four cysteine residues). See also WO 02/057293.

Zinc finger binding domains can be engineered to bind to a target site (see above) using standard techniques. See, Example 1; co-owned U.S. Pat. Nos. 6,453,242 and 6,534,261, including references cited therein. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in co-owned WO 02/077227.

Since an individual zinc finger binds to a three-nucleotide (i.e., triplet) sequence (or a four-nucleotide sequence which can overlap, by one nucleotide, with the four-nucleotide binding site of an adjacent zinc finger), the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. As noted herein, binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain.

In a multi-finger zinc finger binding domain, adjacent zinc fingers can be separated by amino acid linker sequences of approximately 5 amino acids (so-called "canonical" inter-finger linkers) or, alternatively, by one or more non-canonical linkers. See, e.g., co-owned U.S. Pat. Nos. 6,453,242 and 6,534,261. For engineered zinc finger binding domains comprising more than three fingers, insertion of longer ("non-canonical") inter-finger linkers between certain of the zinc fingers may be preferred as it may increase the affinity and/or specificity of binding by the binding domain. See, for example, U.S. Pat. No. 6,479,626 and WO 01/53480. Accordingly, multi-finger zinc finger binding domains can also be characterized with respect to the presence and location of non-canonical inter-finger linkers. For example, a six-finger zinc finger binding domain comprising three fingers (joined by two canonical inter-finger linkers), a long linker and three additional fingers (joined by two canonical inter-finger linkers) is denoted a 2×3 configuration. Similarly, a binding domain comprising two fingers (with a canonical linker therebetween), a long linker and two additional fingers (joined by a canonical linker) is denoted a 2×2 protein. A protein comprising three two-finger units (in each of which the two fingers are joined by a canonical linker), and in which each two-finger unit is joined to the adjacent two finger unit by a long linker, is referred to as a 3×2 protein.

The presence of a long or non-canonical inter-finger linker between two adjacent zinc fingers in a multi-finger binding domain often allows the two fingers to bind to subsites which are not immediately contiguous in the target sequence. Accordingly, there can be gaps of one or more nucleotides between subsites in a target site; i.e., a target site can contain one or more nucleotides that are not contacted by a zinc finger. For example, a 2×2 zinc finger binding domain can bind to two six-nucleotide sequences separated by one nucleotide, i.e., it binds to a 13-nucleotide target site. See also Moore et al. (2001a) Proc. Natl. Acad. Sci. USA 98:1432-1436; Moore et al. (2001b) Proc. Natl. Acad. Sci. USA 98:1437-1441 and WO 01/53480.

As mentioned previously, a target subsite is a three- or four-nucleotide sequence that is bound by a single zinc finger. For certain purposes, a two-finger unit is denoted a binding module. A binding module can be obtained by, for example, selecting for two adjacent fingers in the context of a multi-finger protein (generally three fingers) which bind a particular six-nucleotide target sequence. Alternatively, modules can be constructed by assembly of individual zinc fingers. See also WO 98/53057 and WO 01/53480.

Alternatively, the DNA-binding domain may be derived from a nuclease. For example, the recognition sequences of homing endonucleases and meganucleases such as I-SceI, I-CeuI, PI-PspI, PI-Sce, I-SceIV I-SceIII, I-CreI, I-TevI, I-TevII and I-TevIII are known. See also U.S. Pat. No. 5,420, 032; U.S. Pat. No. 6,833,252; Belfort et al. (1997)*Nucleic Acids Res.* 25:3379-3388; Dujon et al. (1989)*Gene* 82:115-118; Perler et al. (1994)*Nucleic Acids Res.* 22, 1125-1127; Jasin (1996)*Trends Genet.* 12:224-228; Gimble et al. (1996)*J. Mol. Biol.* 263:163-180; Argast et al. (1998)*J Mol. Biol.* 280: 345-353 and the New England Biolabs catalogue. In addition, the DNA-binding specificity of homing endonucleases and meganucleases can be engineered to bind non-natural target sites. See, for example, Chevalier et al. (2002)*Molec. Cell* 10:895-905; Epinat et al. (2003)*Nucleic Acids Res.* 31:2952-2962; Ashworth et al. (2006)*Nature* 441:656-659; Paques et al. (2007)*Current Gene Therapy* 7:49-66; U.S. Patent Publication No. 20070117128.

Cleavage Domains

The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997)*Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases, Cold Spring Harbor Laboratory Press,* 1993). Non limiting examples of homing endonucleases and meganucleases include I-SceI, I-CeuI, PI-PspI, PI-Sce, I-SceIV, I-CsmI, -I-PanI, I-SceI, I-PpoI, I-SceIII, I-CreI, I-TevI, I-TevII and I-TevIII are known. See also U.S. Pat. No. 5,420,032; U.S. Pat. No. 6,833,252; Belfort et al. (1997)*Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. One or more of these enzymes (or functional fragments thereof) can be used as a source of cleavage domains and cleavage half-domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in co-owned International Publication WO 2007/014275, incorporated by reference herein in its entirety.

To enhance cleavage specificity, cleavage domains may also be modified. In certain embodiments, variants of the cleavage half-domain are employed, which variants that minimize or prevent homodimerization of the cleavage half-domains. Non-limiting examples of such modified cleavage half-domains are described in detail in WO 2007/014275, incorporated by reference in its entirety herein. See, also, Examples. In certain embodiments, the cleavage domain comprises an engineered cleavage half-domain (also referred to as dimerization domain mutants) that minimize or prevent homodimerization are known to those of skill the art and described for example in U.S. Patent Publication Nos. 20050064474 and 20060188987, incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Additional engineered cleavage half-domains of Fok I form an obligate heterodimers can also be used in the ZFNs described herein. The first cleavage half-domain includes mutations at amino acid residues at positions 490 and 538 of Fok I and the second cleavage half-domain includes mutations at amino acid residues 486 and 499.

In certain embodiments, the cleavage domain comprises two cleavage half-domains, both of which are part of a single polypeptide comprising a binding domain, a first cleavage half-domain and a second cleavage half-domain. The cleavage half-domains can have the same amino acid sequence or different amino acid sequences, so long as they function to cleave the DNA.

In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In yet another embodiment, two cleavage half-domains are used wherein one of the half domains is enzymatically inactive, such that a single-stranded nick is introduced at the target site (see for example co-owned U.S. provisional application 61/189,800). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotides or more). In general, the point of cleavage lies between the target sites.

DNA-Binding Domain-Cleavage Domain Fusions

Methods for design and construction of fusion proteins (and polynucleotides encoding same) are known to those of skill in the art. For example, methods for the design and construction of fusion protein comprising zinc finger proteins (and polynucleotides encoding same) are described in co-owned U.S. Pat. Nos. 6,453,242 and 6,534,261; and International Publication WO 2007/014275. In certain embodiments, polynucleotides encoding such fusion proteins are constructed. These polynucleotides can be inserted into a vector and the vector can be introduced into a cell (see below for additional disclosure regarding vectors and methods for introducing polynucleotides into cells).

In certain embodiments of the methods described herein, a fusion protein comprises a zinc finger binding domain and a cleavage half-domain from the Fok I restriction enzyme, and two such fusion proteins are expressed in a cell. Expression of two fusion proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a fusion protein comprises a single polypeptide chain comprising two cleavage half domains and a zinc finger binding domain. In this case, a single fusion protein is expressed in a cell and, without wishing to be bound by theory, is believed to cleave DNA as a result of formation of an intramolecular dimer of the cleavage half-domains.

Two fusion proteins, each comprising a zinc finger binding domain and a cleavage half-domain, may be expressed in a cell, and bind to target sites which are juxtaposed in such a way that a functional cleavage domain is reconstituted and DNA is cleaved in the vicinity of the target sites. In one embodiment, cleavage occurs between the target sites of the two zinc finger binding domains. One or both of the zinc finger binding domains and/or cleavage domains can be engineered.

The components of the fusion proteins (e.g., ZFP-Fok I fusions) may be arranged such that the zinc finger domain is nearest the amino terminus of the fusion protein, and the cleavage half-domain is nearest the carboxy-terminus. Dimerization of the cleavage half-domains to form a functional nuclease is brought about by binding of the fusion proteins to sites on opposite DNA strands, with the 5' ends of the binding sites being proximal to each other.

Alternatively, the components of the fusion proteins (e.g., ZFP-Fok I fusions) may be arranged such that the cleavage half-domain is nearest the amino terminus of the fusion protein, and the zinc finger domain is nearest the carboxy-terminus. In these embodiments, dimerization of the cleavage half-domains to form a functional nuclease is brought about by binding of the fusion proteins to sites on opposite DNA strands, with the 3' ends of the binding sites being proximal to each other.

In yet additional embodiments, a first fusion protein contains the cleavage half-domain nearest the amino terminus of the fusion protein, and the zinc finger domain nearest the carboxy-terminus, and a second fusion protein is arranged such that the zinc finger domain is nearest the amino terminus of the fusion protein, and the cleavage half-domain is nearest the carboxy-terminus. In these embodiments, both fusion proteins bind to the same DNA strand, with the binding site of the first fusion protein containing the zinc finger domain nearest the carboxy terminus located to the 5' side of the binding site of the second fusion protein containing the zinc finger domain nearest the amino terminus.

The two fusion proteins can bind in the region of interest in the same or opposite polarity, and their binding sites (i.e., target sites) can be separated by any number of nucleotides, e.g., from 0 to 200 nucleotides or any integral value therebetween. In certain embodiments, the binding sites for two fusion proteins, each comprising a zinc finger binding domain and a cleavage half-domain, can be located between 5 and 18 nucleotides apart, for example, 5-8 nucleotides apart, or 15-18 nucleotides apart, or 6 nucleotides apart, or 16 nucleotides apart, as measured from the edge of each binding site nearest the other binding site, and cleavage occurs between the binding sites.

The site at which the DNA is cleaved generally lies between the binding sites for the two fusion proteins. Double-strand breakage of DNA often results from two single-strand breaks, or "nicks," offset by 1, 2, 3, 4, 5, 6 or more nucleotides, (for example, cleavage of double-stranded DNA by native Fok I results from single-strand breaks offset by 4 nucleotides). Thus, cleavage does not necessarily occur at exactly opposite sites on each DNA strand. In addition, the structure of the fusion proteins and the distance between the target sites can influence whether cleavage occurs adjacent a single nucleotide pair, or whether cleavage occurs at several sites. However, for targeted integration, cleavage within a range of nucleotides is generally sufficient, and cleavage between particular base pairs is not required.

In the disclosed fusion proteins, the amino acid sequence between the zinc finger domain and the cleavage domain (or cleavage half-domain) is denoted the "ZC linker." The ZC linker is to be distinguished from the inter-finger linkers discussed above. ZC linkers are described in detail, for example, in WO 2007/014275.

As discussed in detail below, the fusion protein (ZFN), or a polynucleotide encoding same, is introduced into a cell. Once introduced into, or expressed in, the cell, the fusion protein binds to the target sequence in PPP1R12C and cleaves within this gene locus.

Targeted Integration

The disclosed methods and compositions can be used to cleave DNA in cellular chromatin, which facilitates targeted integration of an exogenous sequence (donor polynucleotide) as described herein. By "integration" is meant both physical insertion (e.g., into the genome of a host cell) and, in addition, integration by copying of the donor sequence into the host cell genome via the nucleic acid replication processes.

For targeted integration, one or more zinc finger binding domains are engineered to bind a target site at or near the predetermined cleavage site, and a fusion protein comprising the engineered zinc finger binding domain and a cleavage domain is expressed in a cell. Upon binding of the zinc finger portion of the fusion protein to the target site, the DNA is cleaved, preferably via a double stranded break, near the target site by the cleavage domain. The presence of a double-stranded break facilitates integration of exogenous sequences as described herein via homologous recombination.

Targeted integration of exogenous sequences, as disclosed herein, can be used to generate cells and cell lines for protein expression. See, for example, co-owned U.S. Patent Application Publication No. 2006/0063231 (the disclosure of which is hereby incorporated by reference herein, in its entirety, for all purposes). For optimal expression of one or more proteins encoded by exogenous sequences integrated into a genome, the chromosomal integration site should be compatible with high-level transcription of the integrated sequences, preferably in a wide range of cell types and developmental states. However, it has been observed that transcription of integrated sequences varies depending on the integration site due to, among other things, the chromatin structure of the genome at the integration site. Accordingly, genomic target sites that support high-level transcription of integrated sequences are desirable. In certain embodiments, it will also be desirable that integration of exogenous sequences not result in ectopic activation of one or more cellular genes (e.g., oncogenes). On the other hand, in the case of integration of promoter and/or enhancer sequences, ectopic expression may be desired.

The exogenous (donor) sequence can be introduced into the cell prior to, concurrently with, or subsequent to, expression of the fusion protein(s).

Methods and compositions are also provided that may enhance levels of targeted recombination including, but not limited to, the use of additional ZFP-functional domain fusions. See, WO 2007/014275.

Further increases in efficiency of targeted recombination, in cells comprising a zinc finger/nuclease fusion molecule and a donor DNA molecule, are achieved by blocking the cells in the $G_2$ phase of the cell cycle, when homology-driven repair processes are maximally active. Such arrest can be achieved in a number of ways. For example, cells can be treated with e.g., drugs, compounds and/or small molecules which influence cell-cycle progression so as to arrest cells in $G_2$ phase. Exemplary molecules of this type include, but are not limited to, compounds which affect microtubule polymerization (e.g., vinblastine, nocodazole, Taxol), compounds that interact with DNA (e.g., cis-platinum(II) diamine dichloride, Cisplatin, doxorubicin) and/or compounds that affect DNA synthesis (e.g., thymidine, hydroxyurea, L-mimosine, etoposide, 5-fluorouracil). Additional increases in recombination efficiency are achieved by the use of histone deacetylase (HDAC) inhibitors (e.g., sodium butyrate, trichostatin A) which alter chromatin structure to make genomic DNA more accessible to the cellular recombination machinery.

Additional methods for cell-cycle arrest include overexpression of proteins which inhibit the activity of the CDK cell-cycle kinases, for example, by introducing a cDNA encoding the protein into the cell or by introducing into the cell an engineered ZFP which activates expression of the gene encoding the protein. Cell-cycle arrest is also achieved by inhibiting the activity of cyclins and CDKs, for example, using RNAi methods (e.g., U.S. Pat. No. 6,506,559) or by introducing into the cell an engineered ZFP which represses expression of one or more genes involved in cell-cycle progression such as, for example, cyclin and/or CDK genes. See, e.g., co-owned U.S. Pat. No. 6,534,261 for methods for the synthesis of engineered zinc finger proteins for regulation of gene expression.

Alternatively, in certain cases, targeted cleavage is conducted in the absence of a donor polynucleotide (preferably in S or $G_2$ phase), and recombination occurs between homologous chromosomes.

Delivery

The nucleic acids as described herein (e.g., a polynucleotide encoding ZFN and/or donor sequence) may be introduced into a cell using any suitable method.

For plant cells, DNA constructs may be introduced into (e.g., into the genome of) a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al (1987) *Nature* 327:70-73). Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al (1984) *Science* 233:496-498, and Fraley et al (1983) *Proc. Nat'l. Acad. Sci. USA* 80:4803.

In addition, gene transfer may be achieved using non-*Agrobacterium* bacteria or viruses such as *Rhizobium* sp. NGR234, *Sinorhizoboium meliloti*, *Mesorhizobium loti*, potato virus X, cauliflower mosaic virus and cassava vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of the construct and adjacent marker into the plant cell DNA when the cell is infected by the bacteria using binary T DNA vector (Bevan (1984) *Nuc. Acid Res.* 12:8711-8721) or the co-cultivation procedure (Horsch et al (1985) *Science* 227:1229-1231). Generally, the *Agrobacterium* transformation system is used to engineer dicotyledonous plants (Bevan et al (1982) *Ann. Rev. Genet* 16:357-384; Rogers et al (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al (1984) *EMBO J* 3:3039-3041; Hooykass-Van Slogteren et al (1984) *Nature* 311:763-764; Grimsley et al (1987) *Nature* 325:1677-179; Boulton et al (1989) *Plant Mol. Biol.* 12:31-40; and Gould et al (1991) *Plant Physiol.* 95:426-434.

Alternative gene transfer and transformation methods include, but are not limited to, protoplast transformation through calcium-, polyethylene:glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

Similarly, the fusion protein(s) (ZFNs) can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any, modified forms or analogues or DNA and/or RNA.

In certain embodiments, one or more ZFPs or ZFP fusion proteins can be cloned into a vector for transformation into prokaryotic or eukaryotic cells for replication and/or expression. Vectors can be prokaryotic vectors, e.g., plasmids, or shuttle vectors, insect vectors, or eukaryotic vectors. A nucleic acid encoding sequences described herein (ZFNs) can also be cloned into an expression vector, for administration to a plant cell, animal cell, preferably a mammalian cell or a human cell, fungal cell, bacterial cell, or protozoal cell using standard techniques described for example in Sambrook et al., supra and United States Patent Publications 20030232410; 20050208489; 20050026157; 20050064474; and 20060188987, and International Publication WO 2007/014275.

In certain embodiments, the ZFNs and donor sequences are delivered in vivo or ex vivo for gene therapy uses. Non-viral vector delivery systems for delivering polynucleotides to cells include DNA plasmids, naked nucleic acid, and nucleic acid complexed with a delivery vehicle such as a liposome or poloxamer. Viral vector delivery systems for delivery of the ZFNs include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids in vivo or ex vivo include electroporation, lipofection (see, U.S. Pat. Nos. 5,049,386; 4,946,787 and commercially available reagents such as Transfectam™ and Lipofectin™), microinjection, biolistics, virosomes, liposomes (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787), immunoliposomes, polycation or lipid:nucleic acid conjugates, naked DNA, artificial virions, viral vector systems (e.g., retroviral, lentivirus, adenoviral, adeno-associated, vaccinia and herpes simplex virus vectors as described in WO 2007/014275 for delivering proteins comprising ZFPs) and agent-enhanced uptake of DNA. Sonoporation using, e.g.; the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.) and BTX Molecular Delivery Systems (Holliston, Mass.).

In certain embodiments, for example, in which transient expression of a ZFP fusion protein is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102

(1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089-(1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the polynucleotides (e.g., ZFN-encoding sequence) be delivered with a high degree of specificity to a particular tissue type. Accordingly, a viral vector can be modified to have specificity for a given cell type by expressing a ligand as a fusion protein with, a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA) and exogenous sequence, and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Tad (differentiated antigen presenting cells) (see Inaba et al., *J. Exp. Med.* 176:1693-1702 (1992)).

In one embodiment, the cell to be used is an oocyte.

In other embodiments, cells derived from model organisms may be used. These can include cells derived from xenopus, insect cells (e.g., drosophilia) and nematode cells.

Vectors (e.g., retroviruses, adenoviruses, liposomes, etc.) comprising nucleic acids as described herein can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to, administer the composition. Accordingly, there is a wide variety of suitable formulations of pharmaceutical compositions available, as described below (see, e.g., *Remington's Pharmaceutical Sciences*, 17th ed., 1989).

As noted above, one or more of the ZFN fusion proteins can be also be introduced into the cell as polypeptides using methods described for example in WO 2007/014275. Non-limiting examples of protein delivery vehicles include, "membrane translocation polypeptides," for example peptide have amphiphilic or hydrophobic amino acid subsequences that have the ability to act as membrane-translocating carriers, toxin molecules, liposomes and liposome derivatives such as immunoliposomes (including targeted liposomes).

ZFPs and expression vectors encoding ZFPs can be administered directly to the patient for targeted cleavage integration into the PPP1R12C locus for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like.

Administration of therapeutically effective amounts is by any of the routes normally used for introducing ZFP into ultimate contact with the tissue to be treated. The ZFPs are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., *Remington's Pharmaceutical Sciences*, 17$^{th}$ ed. 1985)).

The ZFPs, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

Transformed plant cells which are produced by any of the above plant cell transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna, and Zea.

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection may be performed by growing the engineered plant material on media containing an inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

EXAMPLES

Example 1

Design of Linear Donor Constructs

Linear donor constructs with homology arms of 50, 75 or 100 base pairs flanking a sequence encoding a protein of interest were designed and constructed as follows. Donor constructs included homology arms contained within the PPP1R12C locus (also referred to as AAVS1 or p84 site) or within the endogenous IL2Rγ locus. See, U.S. Provisional Application No. 60/926,322, filed Apr. 26, 2007 for a description of the PPP1R12C locus, incorporated by reference in its entirety herein.

Donor constructs were prepared by PCR using primers with 50, 75 or 100 base pairs of homology to the genomic target (PPP1R12C or IL2Rγ). The templates used for these PCRs were plasmid molecules containing two long (approx. 750 bp) fragments homologous to the genomic target, flanking a GFP construct. (GFP constructs are elaborated upon in sections 0139 for AAVS1 and 0140 for IL2Rγ). In addition, the primers were constructed to include phosphorothioate phosphodiester bonds at the first and second phosphodiester bonds of the 5' ends of the primers to protect the linear donor from exonucleolytic degradation. Phosphorothioate phosphodiester bonds were introduced using standard techniques, for example as described in Ciafre et al. (1995) *Nucleic Acids Res.* 23(20):4134-42 and Johansson et al. (2002)*Vaccine* 20(27-28):3379-88.

Alternatively, donor constructs can be prepared by PCR as shown schematically in FIG. 1. Briefly, the donors can be made by PCR using a primer with a 50, 75 or 100 base pair 5' portion homologous to the genomic target (PPP1R12C or IL2Rγ) and a 15-30 base pair portion identical to the open reading frame (ORF) of interest. In addition, the primers can be constructed to include phosphorothioate phosphodiester bonds at the first and second phosphodiester bonds of the 5' ends of the primers to protect the linear donor from exonucleolytic degradation. Phosphorothioate phosphodiester bonds can be introduced using standard techniques, for example as described in Ciafre et al. (1995) *Nucleic Acids Res.* 23(20): 4134-42 and Johansson et al. (2002) *Vaccine* 20(27-28): 3379-88.

PCR primers for constructs containing 50, 75 and 100 base pair homology arms to PPP1R12C are shown in Table 1 and PCR primers for constructs containing 50 base pair homology arms to IL2Rγ are shown in Table 2.

TABLE 1

| PCR primer | Sequence | SEQ ID NO |
|---|---|---|
| AAV-50F | GGCTCTGGTTCTGGGTACTTTTATCTGTCCCCTCCACCC CACAGTGGGGC | 5 |
| AAV-50R | AGGAGGAGGCCTAAGGATGGGGCTTTTCTGTCACCAATC CTGTCCCTAGT | 6 |
| AAV-75F | TTATATTCCCAGGGCCGGTTAATGTGGCTCTGGTTCTGG GTACTTTTATCTGTCCCCTCCACCCCACAGTGGGGC | 7 |
| AAV-75R | TAGACCCAATATCAGGAGACTAGGAAGGAGGAGGCCTAA GGATGGGGCTTTTCTGTCACCAATCCTGTCCCTAGT | 8 |
| AAV-100F | CCTGTGTCCCCGAGCTGGGACCACCTTATATTCCCAGGG CCGGTTAATGTGGCTCTGGTTCTGGGTACTTTTATCTGT CCCCTCCACCCCACAGTGGGGC | 9 |
| AAV-100R | AATCTGCCTAACAGGAGGTGGGGGTTAGACCCAATATCA GGAGACTAGGAAGGAGGAGGCCTAAGGATGGGGCTTTTC TGTCACCAATCCTGTCCCTAGT | 10 |

TABLE 2

| PCR primer | Sequence | SEQ ID NO |
|---|---|---|
| IL-50F | GTGTGGATGGGCAGAAACGCTACACGTTTCGTGTTCGG AGCCGCTTTAAC | 11 |
| IL-50R | TGGATTGGGTGGCTCCATTCACTCCAATGCTGAGCACT TCCACAGAGTGG | 12 |

Multiple PCR reactions were run for each donor construct. Conditions for both AAVS1 and IL2Rγ donor PCRs: 95° C., 3 min→30×[95° C., 30 sec; 72° C., 2 min]→72° C., 5 min→hold 4° C. The reactions were pooled and the constructs purified using QiaQuick™ PCR purification kit (Qiagen) to obtain the constructs shown in FIGS. 2 through 5.

FIGS. 2, 3 and 4 show donor molecules targeted to PPP1R12C (AAVS1). In particular, FIG. 2 shows a linear donor molecule (SEQ ID NO:1) targeted to AAVS1 and having homology arms of 100 base pairs and referred to as AAVS1 100 bp HA donor. The left homology arm of AAVS1 100 bp HA extends from nucleotides 1 to 100 (lowercase, underlined); an SA site extends from nucleotides 107 to 132 (lowercase, bold); a sequence encoding a 2A peptide from nucleotides 141 to 212 (uppercase, no underlining); a sequence encoding green fluorescent protein (GFP) poly(A) extends from nucleotides 219 to 1,215 (uppercase, underlined); and a right homology arm extends from nucleotides 1235 to 1334 (lowercase, underlined).

FIG. 3 shows a linear donor molecule (SEQ ID NO:2) having homology arms of 75 base pairs and designated AAVS1 75 bp HA. In this construct, the left homology arm extends from nucleotides 1 to 75 (lowercase, underlined); an SA site extends from nucleotides 82 to 107 (lowercase, bold); a sequence encoding a 2A peptide from nucleotides 116 to 187 (uppercase, no underlining); a sequence encoding GFP poly(A) extends from nucleotides 194 to 1,190 (uppercase, underlined); and a right homology arm extends from nucleotides 1210 to 1284 (lowercase, underlined).

FIG. 4 shows a linear donor molecule (SEQ ID NO:3) having homology arms of 50 base pairs and designated AAVS1 50 bp HA. AAVS1 50 bp HA comprises a left homology arm from nucleotides 1 to 50 (lowercase, underlined); an SA site from nucleotides 57 to 82 (lowercase, bold); a sequence encoding a 2A peptide from nucleotides 91 to 162 (uppercase, no underlining); a sequence encoding GFP poly (A) from nucleotides 169 to 1,165 (uppercase, underlined); and a right homology arm from nucleotides 1,185 to 1,234 (lowercase, underlined).

The sequence of a donor molecule for IL2Rγ is shown in FIG. 5 (SEQ ID NO:4). This molecule comprises homology arms of 50 base pairs (left homology arm from nucleotides 1 to 50 (lowercase, underlined) and right homology arm from nucleotides 1,639 to 1,688 (lower, underlined)). The IL2Rγ 50 bp HA donor molecule also comprises an hPGK promoter sequence from nucleotides 79 to 594 (lowercase, bold) and a sequence encoding GFP poly(A) from nucleotides 615 to 1,611 (uppercase, underlined).

Example 2

Targeted Integration of Linear Donor Constructs

To evaluate targeted integration of linear donor constructs having short (50-100 base pair) homology arms, the linear donors and a pair of fusion proteins comprising a zinc finger protein nuclease (ZFNs) as described in U.S. Provisional Application No. 60/926,322, filed Apr. 26, 2007 and shown in Table 3 (DNA target sites indicated in uppercase letters; non-contacted nucleotides indicated in lowercase), were transfected into K562 cells using the Amaxa™ Nucleofection kit as shown in Table 4.

TABLE 3

| ZFN Name | Target Site | F1 | F2 | F3 | F4 |
|---|---|---|---|---|---|
| 2189-11 | acTAGGGA CAGGATg (SEQ ID NO: 13) | QSSNLAR (SEQ ID NO: 14) | RPDFLNQ (SEQ ID NO: 15) | QSGHLAR (SEQ ID NO: 16) | RSDNLTT (SEQ ID NO: 17) |
| r2182-8 | ccCCACTG TGGGGTgg (SEQ ID NO: 18) | QSSHLTR (SEQ ID NO: 19) | RSDHLTT (SEQ ID NO: 20) | HNYARDC (SEQ ID NO: 21) | QKATRTT (SEQ ID NO: 22) |

TABLE 4

| Sample # | ZFN target (2.5 μg) | Donor | Donor con'c (μg) |
|---|---|---|---|
| 1 | GFP | none | |
| 2 | no ZFN | SA-2A-GFP-pA (circular) | 50 |
| 3 | no ZFN | 50 bp HA donor | 5 |
| 4 | no ZFN | 75 bp HA donor | 5 |
| 5 | no ZFN | 100 bp HA donor | 5 |
| 6 | no ZFN | 50 bp HA donor | 6.9 |
| 7 | no ZFN | 100 bp HA donor | 7.5 |
| 8 | AAVS1 | SA-2A-GFP-pA (circular) | 50 |

TABLE 4-continued

| Sample # | ZFN target (2.5 μg) | Donor | Donor con'c (μg) |
|---|---|---|---|
| 9 | AAVS1 | 50 bp HA donor | 5 |
| 10 | AAVS1 | 75 bp HA donor | 5 |
| 11 | AAVS1 | 100 bp HA donor | 5 |
| 12 | AAVS1 | 50 bp HA donor | 6.9 |
| 13 | AAVS1 | 100 bp HA donor | 7.5 |

The SA-2A-GFP-pA donor refers to the 1,647 bp circular donor fragment described in U.S. Provisional Application No. 60/926,322, corresponding to positions 60318104-60319750 of PPP1R12C.

Forty eight hours after transfection, the rate of targeted integration (TI) was assayed by a radiolabelled PCR assay and Southern blotting, as described Moehle et al. (2007) Proc. Nat'l Acad. Sci. USA 104:3055-3060.

Figure 7:
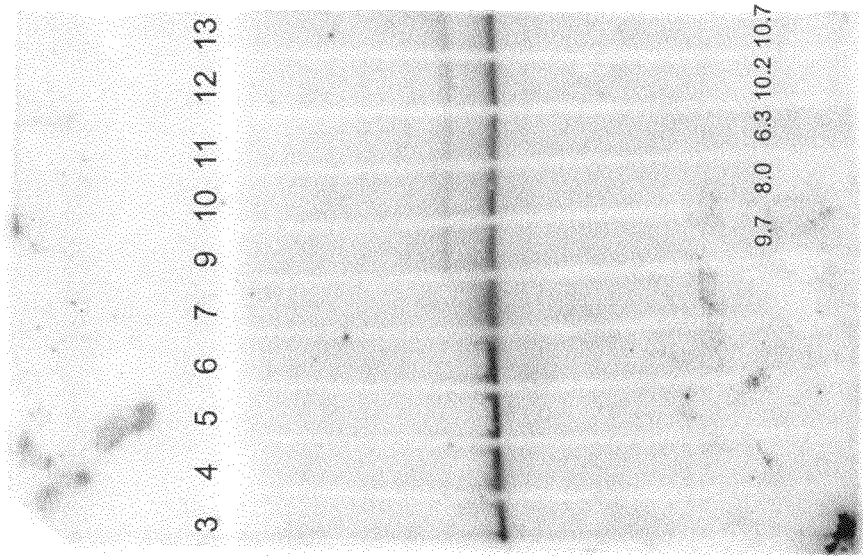
FIG. 7 is a Southern blot showing modification of the PPP1R12C (AAVS1) locus when various donor molecules as described herein are introduced into K562 cells in the absence (lanes 3-7) or presence of AAVS1-targeted ZFNs (lanes 9-13). The percent of chromosomes modified by is listed below lanes 9-13.
Figure 6:
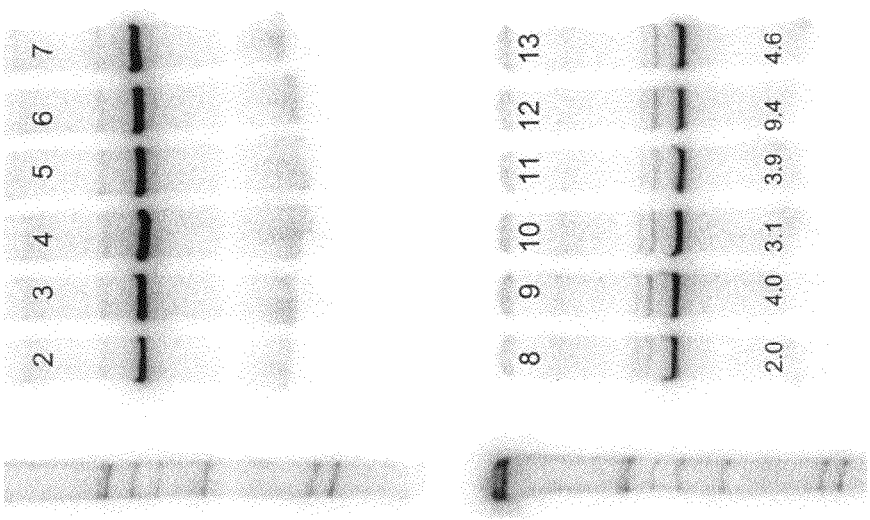
FIG. 6 depicts results of a PCR assay and shows modification of the PPP1R12C (AAVS1) locus when various donor molecules as described herein are introduced into K562 cells in the absence (lanes 2-7) or presence of AAVS1-targeted ZFNs (lanes 8-13).

Results of PCR and Southern blotting are shown in FIG. 6 and FIG. 7, respectively. The top of each lane is marked with the sample number (left column, Table 4) and the percent of chromosomes modified by is listed below each lane.

In addition, one week after transfection, the percentage of GFP-positive cells was assayed by FACS, also as described Moehle et al. (2007).

Figure 8:
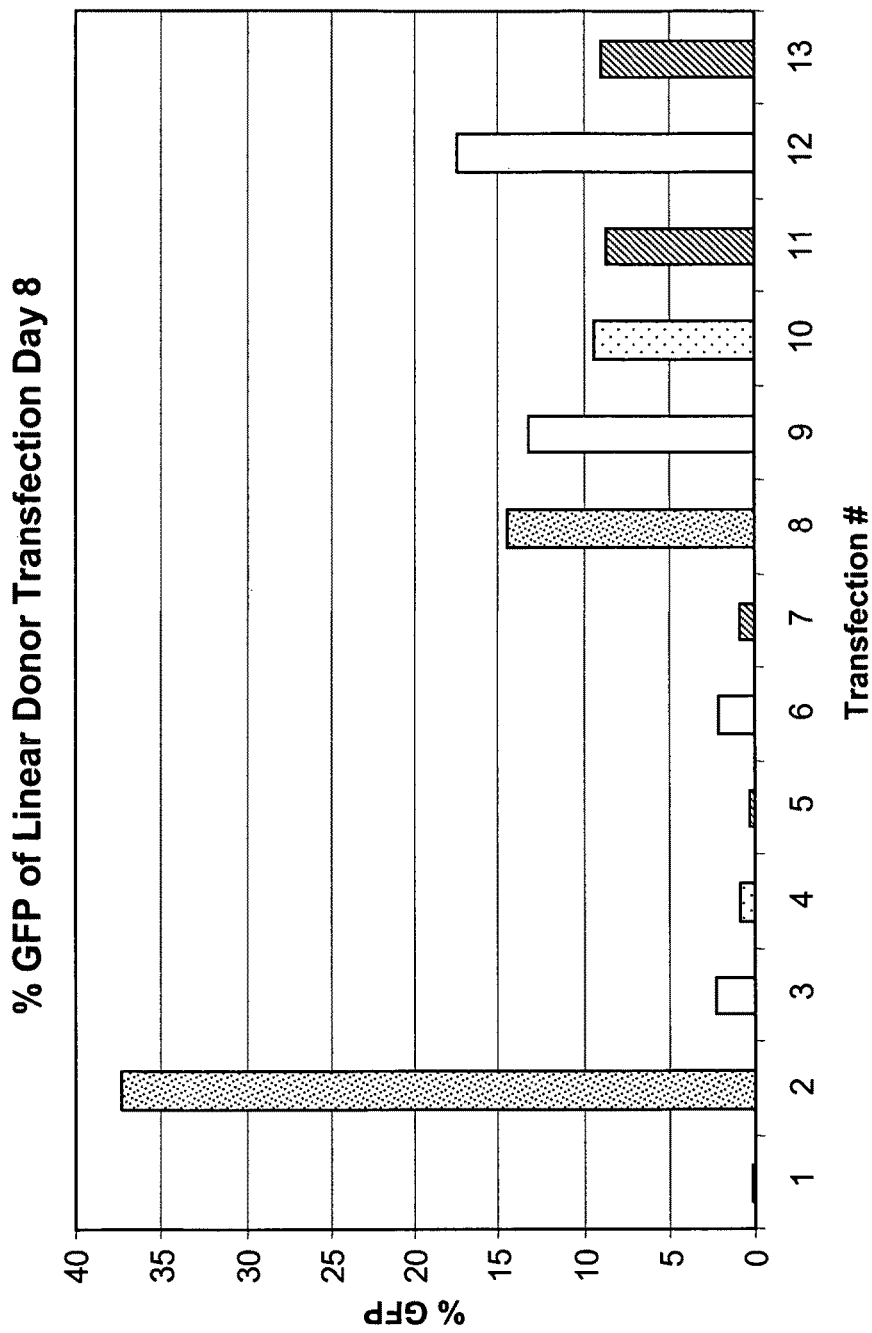
FIG. 8 depicts the percentage of GFP-positive cells as evaluated by FACS.

Results are shown in Table 5 and FIG. 8 and confirm that the GFP ORF of the linear donor sequences was integrated into the genome.

TABLE 5

| | ZFNs (2.5 ug) | Donor | Amount | % GFP | MFI Green | TI % |
|---|---|---|---|---|---|---|
| 1 | GFP | | | 0.21 | 17.99 | 0 |
| 2 | | SA-2A-GFP-pA Donor | 50 ug | 37.28 | 46.32 | 0 |
| 3 | | 50 bp HA Donor | 5 ug | 2.3 | 53.75 | 0 |
| 4 | | 75 bp HA Donor | 5 ug | 0.8 | 29.24 | 0 |
| 5 | | 100 bp HA Donor | 5 ug | 0.28 | 20.81 | 0 |
| 6 | | 50 bp HA Donor | 6.9 ug | 2.07 | 12.51 | 0 |
| 7 | | 100 bp HA Donor | 7.5 ug | 0.81 | 12.21 | 0 |
| 8 | AAVS1 | SA-2A-GFP-pA Donor | 50 ug | 14.47 | 18.1 | 2 |
| 9 | AAVS1 | 50 bp HA Donor | 5 ug | 13.15 | 8.71 | 4 |
| 10 | AAVS1 | 75 bp HA Donor | 5 ug | 9.31 | 7.52 | 3.1 |
| 11 | AAVS1 | 100 bp HA Donor | 5 ug | 8.71 | 8.28 | 3.9 |
| 12 | AAVS1 | 50 bp HA Donor | 6.9 ug | 17.48 | 9.26 | 9.4 |
| 13 | AAVS1 | 100 bp HA Donor | 7.5 ug | 8.91 | 8.71 | 4.6 |

Thus, these results demonstrate that linear donor constructs with short homology arms (~50-100 bp) can be used to efficiently transfer a sequence encoding a polypeptide of interest to a specified genomic location. The linear donor constructs described herein are rapidly generated by PCR using a plasmid template and can be protected from exonucleolytic degradation using phosphorothioate modification.

All patents, patent applications and publications mentioned herein are hereby incorporated by reference, in their entireties, for all purposes.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A linear donor nucleic acid molecule comprising homology arms of between 50 and 100 base pairs, a sequence encoding a 2A peptide and a sequence of interest, wherein the homology arms flank the sequence of interest and the sequence encoding the 2A peptide.

2. The linear donor nucleic acid of claim 1, further comprising, between the homology arms, a sequence comprising an SA site.

3. The linear donor nucleic acid of claim 1, further comprising, between the homology arms, a sequence comprising an IRES sequence.

4. The linear donor nucleic acid of claim 1, wherein the sequence of interest does not encode a polypeptide.

5. The linear donor nucleic acid of claim 1, further comprising a promoter sequence operably linked to the sequence of interest.

6. The linear donor nucleic acid of claim 1, wherein the sequence of interest encodes a polypeptide.

7. The linear donor nucleic acid according to claim 6, wherein the polypeptide is selected from the group consisting of an antibody, an antigen, an enzyme, a growth factor, a cell surface receptor, a nuclear receptor, a hormone, a lymphokine, a cytokine, a reporter gene, a selectable marker, a secreted factor, an epitope tag and functional fragments thereof and combinations thereof.

8. The linear donor nucleic acid of claim 1, wherein the sequence contains a non-coding nucleic acid.

9. The linear donor nucleic acid according to claim 8, wherein the non-coding nucleic acid is selected from the group consisting of a miRNA, and SH-RNA, or siRNA.

10. A method for homology-dependent targeted integration of a sequence of interest into a region of interest in the genome of a cell, the method comprising the steps of:
   (a) expressing a fusion protein in the cell, the fusion protein comprising a DNA-binding domain and cleavage domain or a cleavage half-domain, wherein the DNA-binding domain has been engineered to bind to a target site in the region of interest;
   (b) contacting the cell with a donor polynucleotide of claim 1,
   wherein binding of the fusion protein to the target site cleaves the genome of the cell in the region of the interest, thereby resulting in homology-dependent targeted integration of the sequence of interest into the genome of the cell.

11. A method for homology-dependent targeted integration of a sequence of interest into a cell, the method comprising:
   (a) expressing a first fusion protein in the cell, the first fusion protein comprising a first DNA-binding domain and a first cleavage half-domain, wherein the first DNA-binding domain has been engineered to bind to a first target site in a region of interest in the genome of the cell;
   (b) expressing a second fusion protein in the cell, the second fusion protein comprising a second DNA-domain and a second cleavage half domain, wherein the second zinc finger binding domain binds to a second target site in the region of interest in the genome of the cell, wherein the second target site is different from the first target site; and
   (c) contacting the cell with a polynucleotide comprising a donor nucleic acid according to claim 1;
   wherein binding of the first fusion protein to the first target site, and binding of the second fusion protein to the second target site, positions the cleavage half-domains such that the genome of the cell is cleaved in the region of interest, thereby resulting in homology-dependent integration of the donor nucleic said into the genome of the cell.

12. The method of claim 10, wherein at least one DNA-binding domain is a zinc finger binding domain.

13. The method of claim 10, wherein at least one DNA-binding domain is a meganuclease DNA-binding domain.

14. The method of claim 10, wherein the sequence of interest from the integrated donor nucleic acid expresses a polypeptide.

15. The method of claim 10, wherein the sequence in interest from the integrated donor comprises a non-coding nucleic acid sequence.

16. The method of claim 10, wherein the cleavage domain is from a meganuclease.

17. The method of claim 11, wherein the first and second cleavage half-domains are from a Type IIS restriction endonuclease.

18. The method according to claim 17, wherein the Type IIS restriction endonuclease is selected from the group consisting of FokI and StsI.

19. The method according to claim 10, wherein the cell is arrested in the G2 phase of the cell cycle.

20. The method according to claim 10, wherein at least one of the fusion proteins comprises an alteration in the amino acid sequence of the dimerization interface of the cleavage half-domain.

21. The method according to claim 10, wherein the cell is a mammalian cell.

22. The method according to claim 10, wherein the cell is a human cell.

23. The method according to claim 10, wherein the cell is a plant cell.

* * * * *

SEQUENCE LISTING

<160> NUMBER OF SEQ ID NOS: 22

<210> SEQ ID NO 1
<211> LENGTH: 1334
<212> TYPE: DNA
<213> ORGANISM: Artificial Sequence
<220> FEATURE:
<223> OTHER INFORMATION: Chemically synthesized sequence: AAVS1 100 bp
      HA

<400> SEQUENCE: 1

```
cctgtgtccc cgagctggga ccaccttata ttcccagggc cggttaatgt ggctctggtt      60
ctgggtactt ttatctgtcc cctccacccc acagtggggc aagcttctga cctcttctct    120
tcctcccaca gggcctcgag agatctggca gcggagaggg cagaggaagt cttctaacat    180
gcggtgacgt ggaggagaat cccggcccta ggctcgagat ggtgagcaag ggcgaggagc    240
tgttcaccgg ggtggtgccc atcctggtcg agctggacgg cgacgtaaac ggccacaagt    300
tcagcgtgtc cggcgagggc gagggcgatg ccacctacgg caagctgacc ctgaagttca    360
tctgcaccac cggcaagctg cccgtgccct ggcccaccct cgtgaccacc ctgacctacg    420
gcgtgcagtg cttcagccgc taccccgacc acatgaagca gcacgacttc ttcaagtccg    480
ccatgcccga aggctacgtc caggagcgca ccatcttctt caaggacgac ggcaactaca    540
agacccgcgc cgaggtgaag ttcgagggcg acaccctggt gaaccgcatc gagctgaagg    600
gcatcgactt caaggaggac ggcaacatcc tggggcacaa gctggagtac aactacaaca    660
gccacaacgt ctatatcatg gccgacaagc agaagaacgg catcaaggtg aacttcaaga    720
tccgccacaa catcgaggac ggcagcgtgc agctcgccga ccactaccag cagaacaccc    780
ccatcggcga cggccccgtg ctgctgcccg acaaccacta cctgagcacc cagtccgccc    840
tgagcaaaga ccccaacgag aagcgcgatc acatggtcct gctggagttc gtgaccgccg    900
ccgggatcac tctcggcatg gacgagctgt acaagtaaag cggccgcgtc gagtctagag    960
ggcccgttta acccgctga tcagcctcga ctgtgccttc tagttgccag ccatctgttg   1020
tttgcccctc ccccgtgcct tccttgaccc tggaaggtgc cactcccact gtcctttcct   1080
aataaaatga ggaaattgca tcgcattgtc tgagtaggtg tcattctatt ctgggggtg    1140
gggtggggca ggacagcaag ggggaggatt gggaagacaa tagcaggcat gctgggatg    1200
cggtgggctc tatgggtcga cagtactaag ctttactagg gacaggattg gtgacagaaa   1260
agccccatcc ttaggcctcc tccttcctag tctcctgata ttgggtctaa ccccacctc    1320
ctgttaggca gatt                                                    1334
```

<210> SEQ ID NO 2
<211> LENGTH: 1284
<212> TYPE: DNA
<213> ORGANISM: Artificial Sequence
<220> FEATURE:
<223> OTHER INFORMATION: Chemically synthesized sequence: AAVS1 75 bp HA

<400> SEQUENCE: 2

```
ttatattccc agggccggtt aatgtggctc tggttctggg tacttttatc tgtcccctcc      60
accccacagt ggggcaagct tctgacctct tctcttcctc ccacagggcc tcgagagatc    120
tggcagcgga gagggcagag gaagtcttct aacatgcggt gacgtggagg agaatcccgg    180
ccctaggctc gagatggtga gcaagggcga ggagctgttc accggggtgg tgcccatcct    240
ggtcgagctg gacggcgacg taaacggcca caagttcagc gtgtccggcg agggcgaggg    300
```

```
cgatgccacc tacggcaagc tgaccctgaa gttcatctgc accaccggca agctgcccgt      360
gccctggccc accctcgtga ccaccctgac ctacggcgtg cagtgcttca gccgctaccc      420
cgaccacatg aagcagcacg acttcttcaa gtccgccatg cccgaaggct acgtccagga      480
gcgcaccatc ttcttcaagg acgacggcaa ctacaagacc cgcgccgagg tgaagttcga      540
gggcgacacc ctggtgaacc gcatcgagct gaagggcatc gacttcaagg aggacggcaa      600
catcctgggg cacaagctgg agtacaacta caacagccac aacgtctata tcatggccga      660
caagcagaag aacggcatca aggtgaactt caagatccgc cacaacatcg aggacggcag      720
cgtgcagctc gccgaccact accagcagaa caccccatc ggcgacggcc ccgtgctgct       780
gcccgacaac cactacctga gcacccagtc cgccctgagc aaagacccca cgagaagcg       840 cgatcacatg gtcctgctgg agttcgtgac cgccgcgggg atcactctcg gcatggacga      900
gctgtacaag taaagcggcc gcgtcgagtc tagagggccc gtttaaaccc gctgatcagc      960
ctcgactgtg ccttctagtt gccagccatc tgttgtttgc ccctccccg tgccttcctt      1020 gaccctggaa ggtgccactc ccactgtcct ttcctaataa aatgaggaaa ttgcatcgca     1080
ttgtctgagt aggtgtcatt ctattctggg gggtggggtg gggcaggaca gcaagggga    1140 ggattgggaa gacaatagca ggcatgctgg ggatgcggtg ggctctatgg gtcgacagta    1200
ctaagcttta ctaggacag gattggtgac agaaaagccc catccttagg cctcctcctt   1260
cctagtctcc tgatattggg tcta                                            1284

<210> SEQ ID NO 3
<211> LENGTH: 1234
<212> TYPE: DNA
<213> ORGANISM: Artificial Sequence
<220> FEATURE:
<223> OTHER INFORMATION: Chemically synthesized sequence: AAVS1 50 bp HA

<400> SEQUENCE: 3
ggctctggtt ctgggtactt ttatctgtcc cctccacccc acagtggggc aagcttctga       60
cctcttctct tcctcccaca gggcctcgag agatctggca gcggagaggg cagaggaagt     120
cttctaacat gcggtgacgt ggaggagaat cccggcccta ggctcgagat ggtgagcaag     180
ggcgaggagc tgttcaccgg ggtggtgccc atcctggtcg agctggacgg cgacgtaaac     240
ggccacaagt tcagcgtgtc cggcgagggc gagggcgatg ccacctacgg caagctgacc     300
ctgaagttca tctgcaccac cggcaagctg cccgtgccct ggcccaccct cgtgaccacc     360
ctgacctacg gcgtgcagtg cttcagccgc taccccgacc acatgaagca gcacgacttc     420
ttcaagtccg ccatgcccga aggctacgtc caggagcgca ccatcttctt caaggacgac     480
ggcaactaca agacccgcgc cgaggtgaag ttcgagggcg acaccctggt gaaccgcatc     540
gagctgaagg gcatcgactt caaggaggac ggcaacatcc tggggcacaa gctggagtac     600
aactacaaca gccacaacgt ctatatcatg gccgacaagc agaagaacgg catcaaggtg     660
aacttcaaga tccgccacaa catcgaggac ggcagcgtgc agctcgccga ccactaccag     720
cagaacaccc ccatcggcga cggccccgtg ctgctgcccg acaaccacta cctgagcacc     780
cagtccgccc tgagcaaaga ccccaacgag aagcgcgatc acatggtcct gctggagttc     840
gtgaccgccg ccgggatcac tctcggcatg gacgagctgt acaagtaaag cggccgcgtc     900
gagtctagag ggcccgttta aacccgctga tcagcctcga ctgtgccttc tagttgccag     960
ccatctgttg tttgccccte ccccgtgcct tccttgaccc tggaaggtgc cactcccact    1020 gtccttttcct aataaaatga ggaaattgca tcgcattgtc tgagtaggtg tcattctatt   1080
```

```
ctgggggtg gggtgggca ggacagcaag ggggaggatt gggaagacaa tagcaggcat    1140
gctggggatg cggtgggctc tatgggtcga cagtactaag ctttactagg gacaggattg    1200
gtgacagaaa agccccatcc ttaggcctcc tcct                                1234
```

<210> SEQ ID NO 4
<211> LENGTH: 1688
<212> TYPE: DNA
<213> ORGANISM: Artificial Sequence
<220> FEATURE:
<223> OTHER INFORMATION: Chemically synthesized sequence: IL2R 50bpHA

<400> SEQUENCE: 4

```
gtgtggatgg gcagaaacgc tacacgtttc gtgttcggag ccgctttaac ctcgatcgag      60
aagcttgata tcgaattccc acggggttgg ggttgcgcct tttccaaggc agccctgggt     120
ttgcgcaggg acgcggctgc tctgggcgtg gttccgggaa acgcagcggc gccgaccctg     180
ggtctcgcac attcttcacg tccgttcgca gcgtcacccg gatcttcgcc gctacccttg     240
tgggcccccc ggcgacgctt cctgctccgc ccctaagtcg ggaaggttcc ttgcggttcg     300
cggcgtgccg gacgtgacaa acggaagccg cacgtctcac tagtaccctc gcagacggac     360
agcgccaggg agcaatggca gcgcgccgac cgcgatgggc tgtggccaat gcggctgct     420 cagcggggcg cgccgagagc agcggccggg aaggggcggt gcgggaggcg gggtgtgggg     480
cggtagtgtg ggccctgttc ctgcccgcgc ggtgttccgc attctgcaag cctccggagc     540
gcacgtcggc agtcggctcc ctcgttgacc gaatcaccga cctctctccc caggggggatc     600 caccggtcgc caccatggtg agcaagggcg aggagctgtt caccggggtg gtgcccatcc     660
tggtcgagct ggacggcgac gtaaacggcc acaagttcag cgtgtccggc gagggcgagg     720
gcgatgccac ctacggcaag ctgaccctga gttcatctg caccaccggc aagctgcccg     780
tgccctggcc cacctcgtg accacccctga cctacggcgt gcagtgcttc agccgctacc     840
ccgaccacat gaagcagcac gacttcttca gtccgccat gcccgaaggc tacgtccagg     900
agcgcaccat cttcttcaag gacgacggca actacaagac ccgcgccgag gtgaagttcg     960
agggcgacac cctggtgaac cgcatcgagc tgaagggcat cgacttcaag gaggacggca    1020
acatcctggg gcacaagctg gagtacaact acaacagcca caacgtctat atcatggccg    1080
acaagcagaa gaacggcatc aaggtgaact tcaagatccg ccacaacatc gaggacggca    1140
gcgtgcagct cgccgaccac taccagcaga cacccccat cggcgacggc cccgtgctgc    1200
tgcccgacaa ccactacctg agcacccagt ccgccctgag caaagacccc aacgagaagc    1260
gcgatcacat ggtcctgctg gagttcgtga ccgccgccgg gatcactctc ggcatggacg    1320
agctgtacaa gtaaagcggc cgcgtcgagt ctagagggcc cgtttaaacc cgctgatcag    1380
cctcgactgt gccttctagt tgccagccat ctgttgtttg cccctccccc gtgccttcct    1440
tgaccctgga aggtgccact cccactgtcc tttcctaata aaatgaggaa attgcatcgc    1500
attgtctgag taggtgtcat tctattctgg ggggtggggt ggggcaggac agcaagggg    1560 aggattggga agacaatagc aggcatgctg gggatgcggt gggctctatg gcttctgagg    1620
cggaaagaac cagtcgagcc actctgtgga agtgctcagc attggagtga atggagccac    1680
ccaatcca                                                              1688
```

<210> SEQ ID NO 5
<211> LENGTH: 50
<212> TYPE: DNA

<213> ORGANISM: Artificial Sequence
<220> FEATURE:
<223> OTHER INFORMATION: Synthetic primer AAV-50F

<400> SEQUENCE: 5
ggctctggtt ctgggtactt ttatctgtcc cctccacccc acagtggggc           50

<210> SEQ ID NO 6
<211> LENGTH: 50
<212> TYPE: DNA
<213> ORGANISM: Artificial Sequence
<220> FEATURE:
<223> OTHER INFORMATION: Synthetic primer AAV-50R

<400> SEQUENCE: 6
aggaggaggc ctaaggatgg ggcttttctg tcaccaatcc tgtccctagt           50

<210> SEQ ID NO 7
<211> LENGTH: 75
<212> TYPE: DNA
<213> ORGANISM: Artificial Sequence
<220> FEATURE:
<223> OTHER INFORMATION: Synthetic primer AAV-75F

<400> SEQUENCE: 7
ttatattccc agggccggtt aatgtggctc tggttctggg tacttttatc tgtcccctcc    60
accccacagt ggggc                                                    75

<210> SEQ ID NO 8
<211> LENGTH: 75
<212> TYPE: DNA
<213> ORGANISM: Artificial Sequence
<220> FEATURE:
<223> OTHER INFORMATION: Synthetic primer AAV-75R

<400> SEQUENCE: 8
tagacccaat atcaggagac taggaaggag gaggcctaag gatggggctt ttctgtcacc    60
aatcctgtcc ctagt                                                    75

<210> SEQ ID NO 9
<211> LENGTH: 100
<212> TYPE: DNA
<213> ORGANISM: Artificial Sequence
<220> FEATURE:
<223> OTHER INFORMATION: Synthetic primer AAV-100F

<400> SEQUENCE: 9
cctgtgtccc cgagctggga ccaccttata ttcccagggc cggttaatgt ggctctggtt    60
ctgggtactt ttatctgtcc cctccacccc acagtggggc                        100

<210> SEQ ID NO 10
<211> LENGTH: 100
<212> TYPE: DNA
<213> ORGANISM: Artificial Sequence
<220> FEATURE:
<223> OTHER INFORMATION: Synthetic primer AAV-100R

<400> SEQUENCE: 10
aatctgccta acaggaggtg ggggttagac ccaatatcag gagactagga aggaggaggc    60
ctaaggatgg ggcttttctg tcaccaatcc tgtccctagt                        100

<210> SEQ ID NO 11
<211> LENGTH: 50

```
<212> TYPE: DNA
<213> ORGANISM: Artificial Sequence
<220> FEATURE:
<223> OTHER INFORMATION: Synthetic primer IL-50F

<400> SEQUENCE: 11
gtgtggatgg gcagaaacgc tacacgtttc gtgttcggag ccgctttaac          50

<210> SEQ ID NO 12
<211> LENGTH: 50
<212> TYPE: DNA
<213> ORGANISM: Artificial Sequence
<220> FEATURE:
<223> OTHER INFORMATION: Synthetic primer IL-50R

<400> SEQUENCE: 12
tggattgggt ggctccattc actccaatgc tgagcacttc cacagagtgg          50

<210> SEQ ID NO 13
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 13
actagggaca ggattg                                              16

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Gln Ser Ser Asn Leu Ala Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Arg Pro Asp Phe Leu Asn Gln
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Gln Ser Gly His Leu Ala Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide
```

<400> SEQUENCE: 17

Arg Ser Asp Asn Leu Thr Thr
1               5

<210> SEQ ID NO 18
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 18
ccccactgtg gggtgg                                                      16

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Gln Ser Ser His Leu Thr Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

Arg Ser Asp His Leu Thr Thr
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide

<400> SEQUENCE: 21

His Asn Tyr Ala Arg Asp Cys
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide

<400> SEQUENCE: 22

Gln Lys Ala Thr Arg Thr Thr
1               5